(12) United States Patent
Zhou

(10) Patent No.: US 12,144,893 B2
(45) Date of Patent: Nov. 19, 2024

(54) COMPOSITION OF MULTIVITAMIN FOR STIMULATING GASTROINTESTINAL SYSTEM MOTILITY AND PREPARATION METHOD THEREFOR

(71) Applicant: Zensun (Shanghai) Science & Technology, Co., Ltd., Shanghai (CN)

(72) Inventor: Mingdong Zhou, New South Wales (AU)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 527 days.

(21) Appl. No.: 17/057,058

(22) PCT Filed: Apr. 23, 2019

(86) PCT No.: PCT/CN2019/083786
§ 371 (c)(1),
(2) Date: Nov. 19, 2020

(87) PCT Pub. No.: WO2019/206107
PCT Pub. Date: Oct. 31, 2019

(65) Prior Publication Data
US 2021/0393531 A1    Dec. 23, 2021

(30) Foreign Application Priority Data

Apr. 28, 2018 (CN) .......................... 201810400340.1
Jan. 31, 2019 (CN) .......................... 201910099043.2
Apr. 18, 2019 (CN) .......................... 201910313858.6

(51) Int. Cl.
*A61K 9/24*   (2006.01)
*A61K 9/20*   (2006.01)
(Continued)

(52) U.S. Cl.
CPC ............ *A61K 9/209* (2013.01); *A61K 9/2095* (2013.01); *A61K 31/197* (2013.01);
(Continued)

(58) Field of Classification Search
None
See application file for complete search history.

(56) References Cited

U.S. PATENT DOCUMENTS

2010/0203126 A1* 8/2010 Park ...................... A61K 9/2054
                                                          514/552
2017/0281666 A1* 10/2017 Chang ................ A61K 31/4188
2018/0353469 A1* 12/2018 Zhou .................... A61K 31/375

FOREIGN PATENT DOCUMENTS

CN          1863811 A        11/2006
CN       101801364 A         8/2010
(Continued)

OTHER PUBLICATIONS

Machine translation, WO 2016/197889 (Year: 2016).*
(Continued)

*Primary Examiner* — Bethany P Barham
*Assistant Examiner* — Barbara S Frazier
(74) *Attorney, Agent, or Firm* — SHEPPARD, MULLIN, RICHTER & HAMPTON LLP

(57) ABSTRACT

The present invention relates to a composition of a multivitamin, vitamins B and C, and a preparation method therefor, and in particular, to a composition of a multivitamin, vitamins B and C for stimulating gastrointestinal system motility and a preparation method therefor. The composition is suitable for preventing and/or treating the statuses or diseases related to a lack of gastrointestinal motility.

5 Claims, 8 Drawing Sheets

Effects of single dose of 9 components multivitamin BC on the small intestinal propulsive rate in mice with loperamide-induced constipation.

(51) Int. Cl.
| | |
|---|---|
| *A61K 31/197* | (2006.01) |
| *A61K 31/375* | (2006.01) |
| *A61K 31/4188* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/714* | (2006.01) |
| *A61P 1/14* | (2006.01) |

(52) U.S. Cl.
CPC ........ *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/714* (2013.01); *A61P 1/14* (2018.01)

(56) References Cited

FOREIGN PATENT DOCUMENTS

| | | |
|---|---|---|
| CN | 102302512 A | 1/2012 |
| CN | 104337813 A | 2/2015 |
| CN | 104936581 A | 9/2015 |
| CN | 106265696 A | 1/2017 |
| EP | 3308787 A1 | 4/2018 |
| EP | 3545960 A1 | 10/2019 |
| WO | WO 2006108208 A1 | 10/2006 |
| WO | WO-2016197889 A1 * 12/2016 ............. A23L 33/15 |
| WO | WO 2017149392 A1 | 9/2017 |

OTHER PUBLICATIONS

Bao Qi'an, "Functions of Beer," Liquor-Making Science and Technology, vol. 114, No. 6, Dec. 31, 2002 (Dec. 31, 2002), pp. 29-31, ISSN: 1001-9286.

* cited by examiner

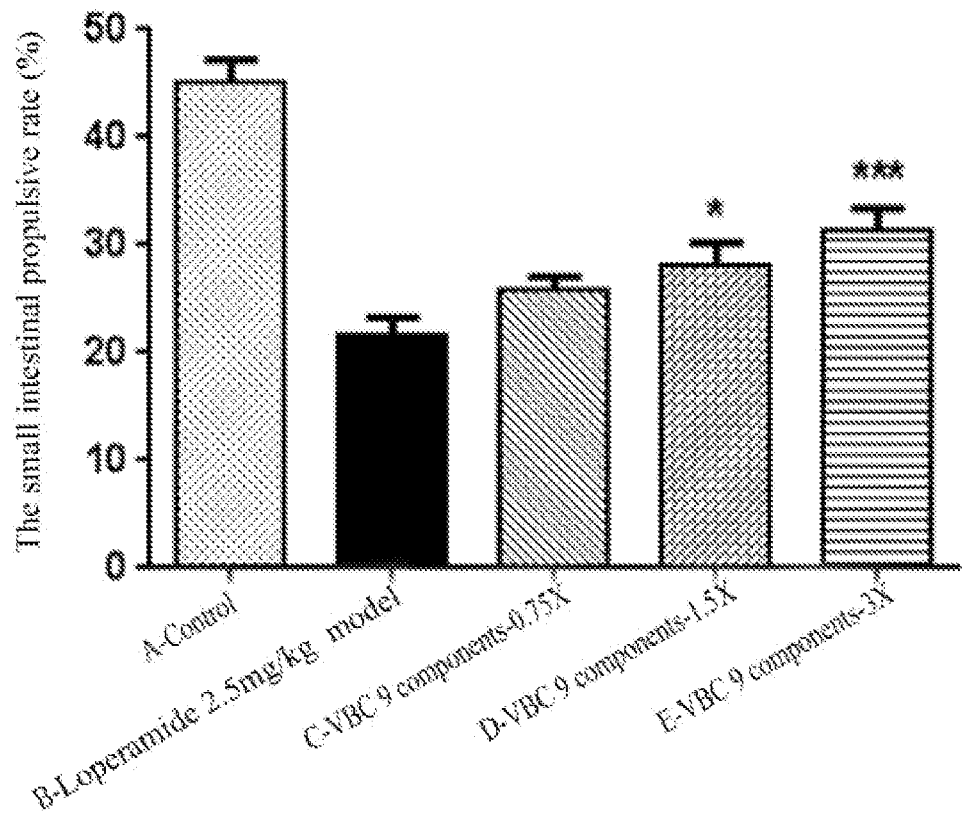
Figure 1: Effects of single dose of 9 components multivitamin BC on the small intestinal propulsive rate in mice with loperamide-induced constipation.

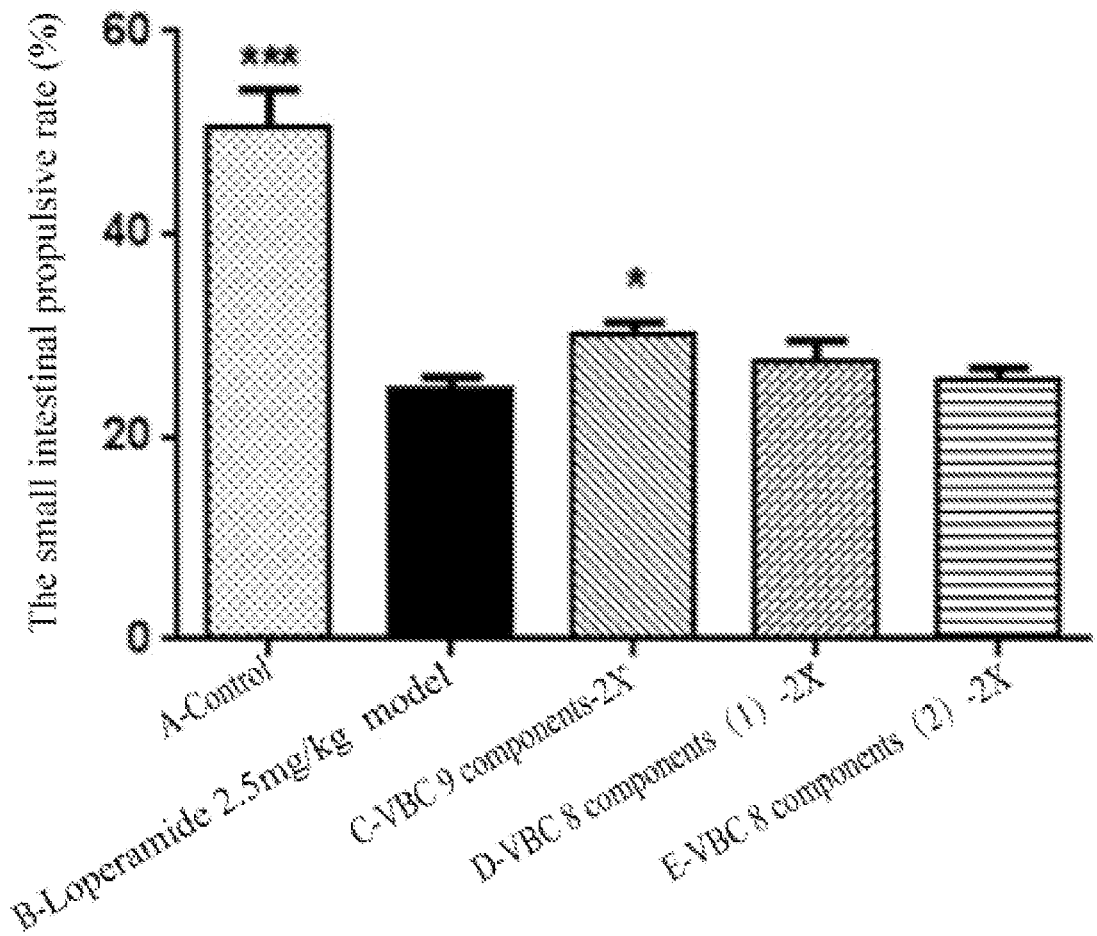
Figure 2: Effects of single dose of combination 1 or combination 2 (8 components multivitamin BC) on the small intestinal propulsive rate in mice with loperamide-induced constipation.

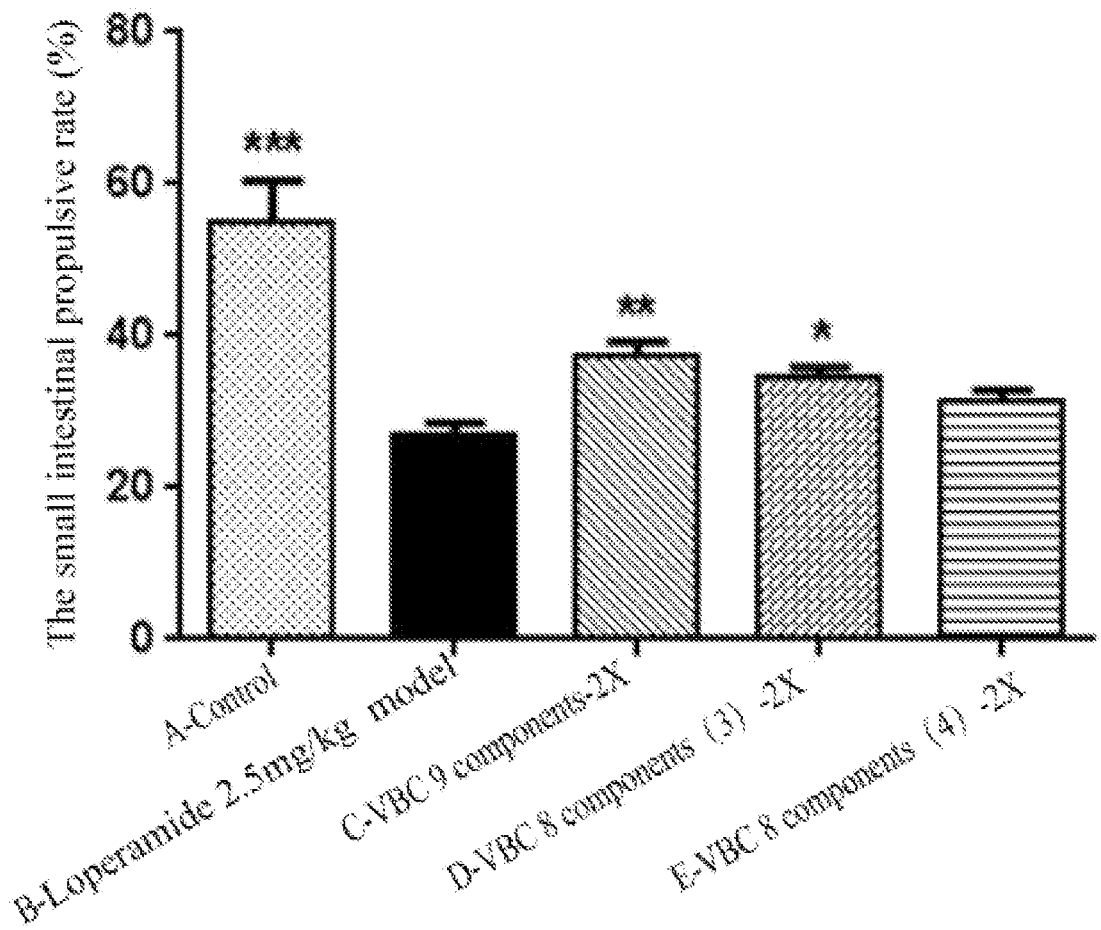
Figure 3: Effects of single dose of combination 3 or combination 4 (8 components multivitamin BC) on the small intestinal propulsive rate in mice with loperamide-induced constipation.

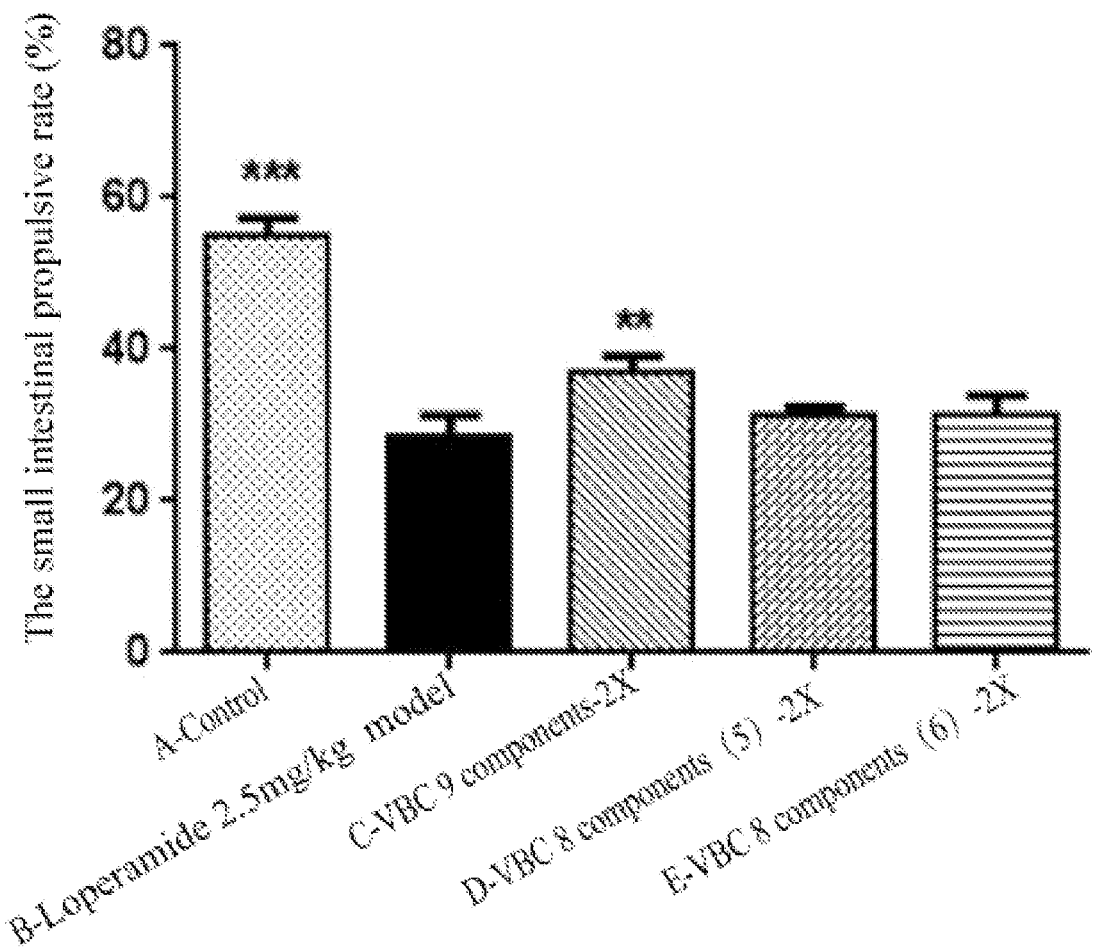
Figure 4: Effects of single dose of combination 5 or combination 6 (8 components multivitamin BC) on the small intestinal propulsive rate in mice with loperamide-induced constipation.

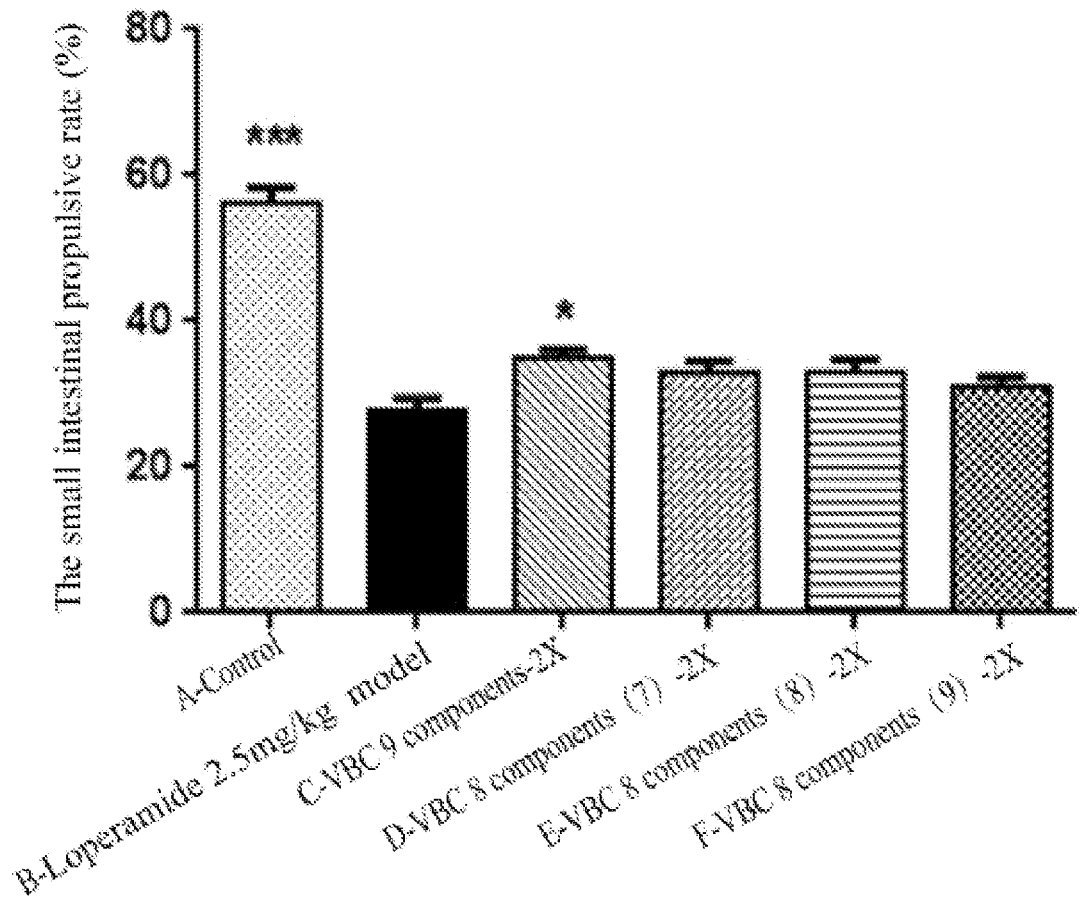
Figure 5: Effects of single dose of combination 7, combination 8 or combination 9 (8 components multivitamin BC) on the small intestinal propulsive rate in mice with loperamide-induced constipation.

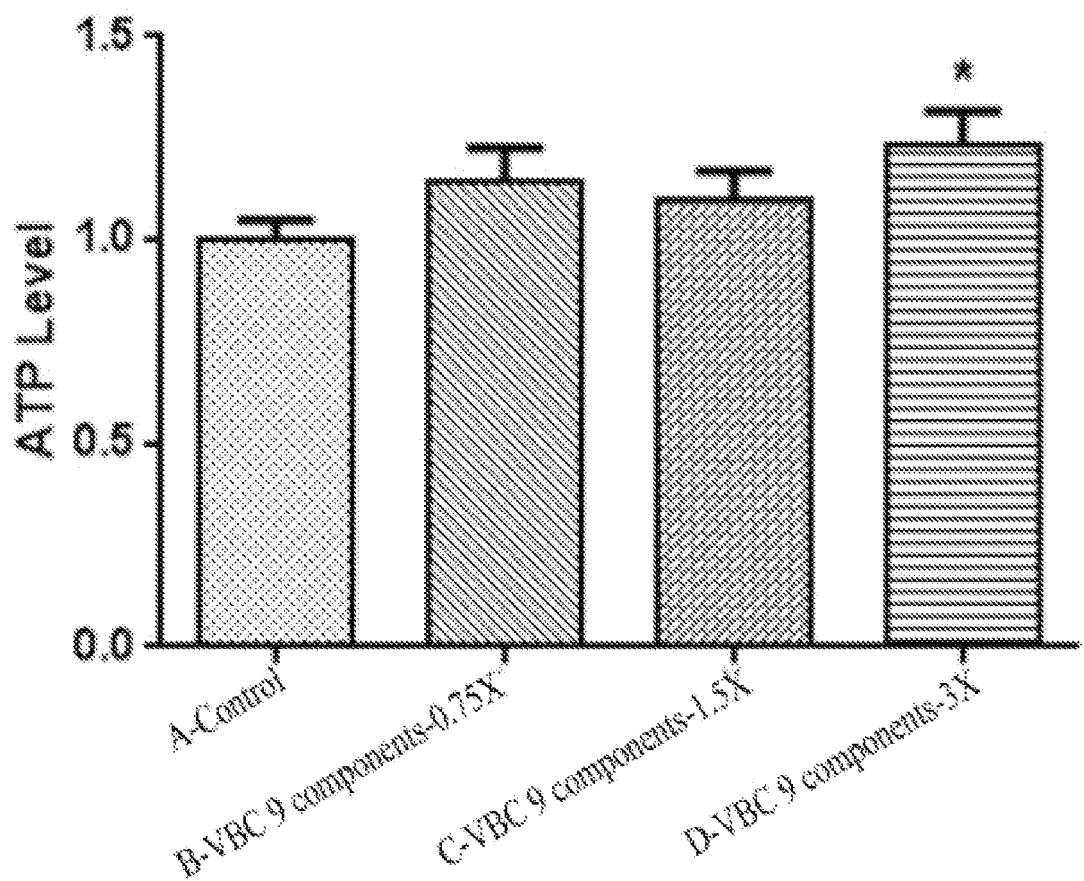
Figure 6: Effects of single dose of multivitamin BC on the ATP content of energy metabolism of small intestinal in mice.

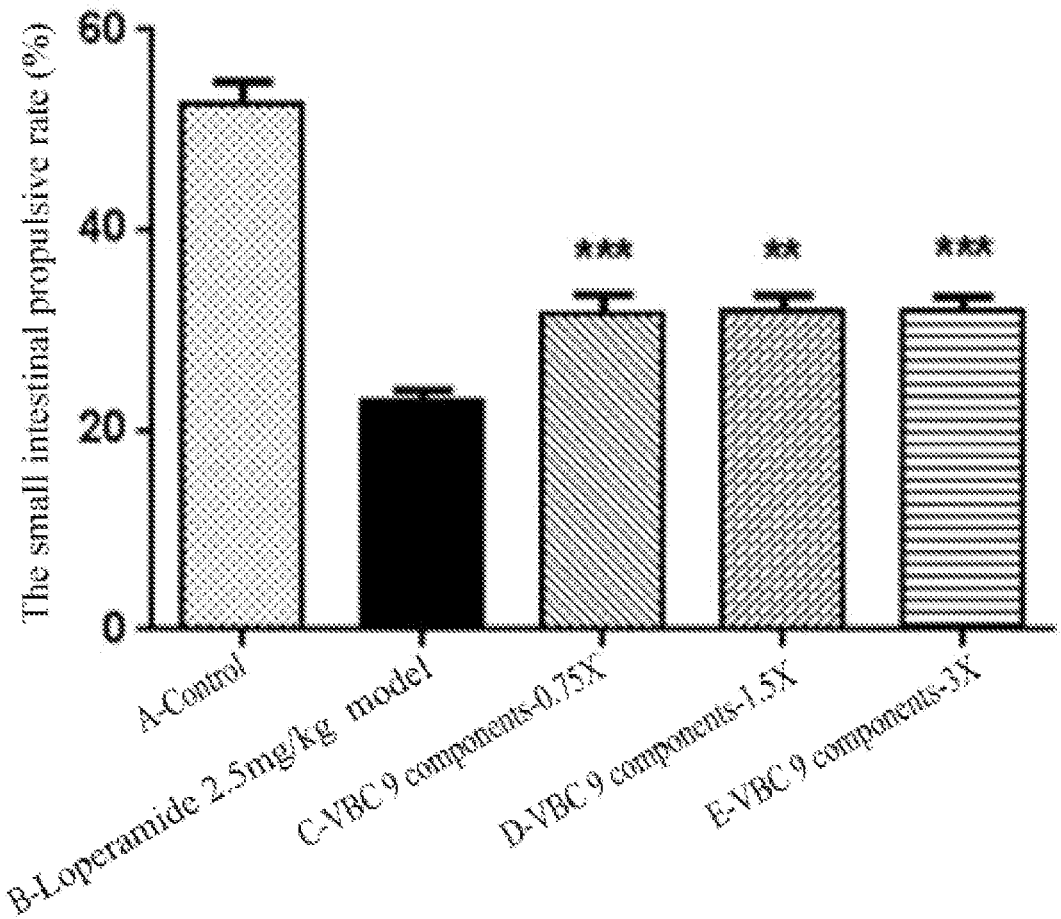
Figure 7. Effects of multiple doses of multivitamin BC on small intestine propulsion function in mice with loperamide-induced constipation.

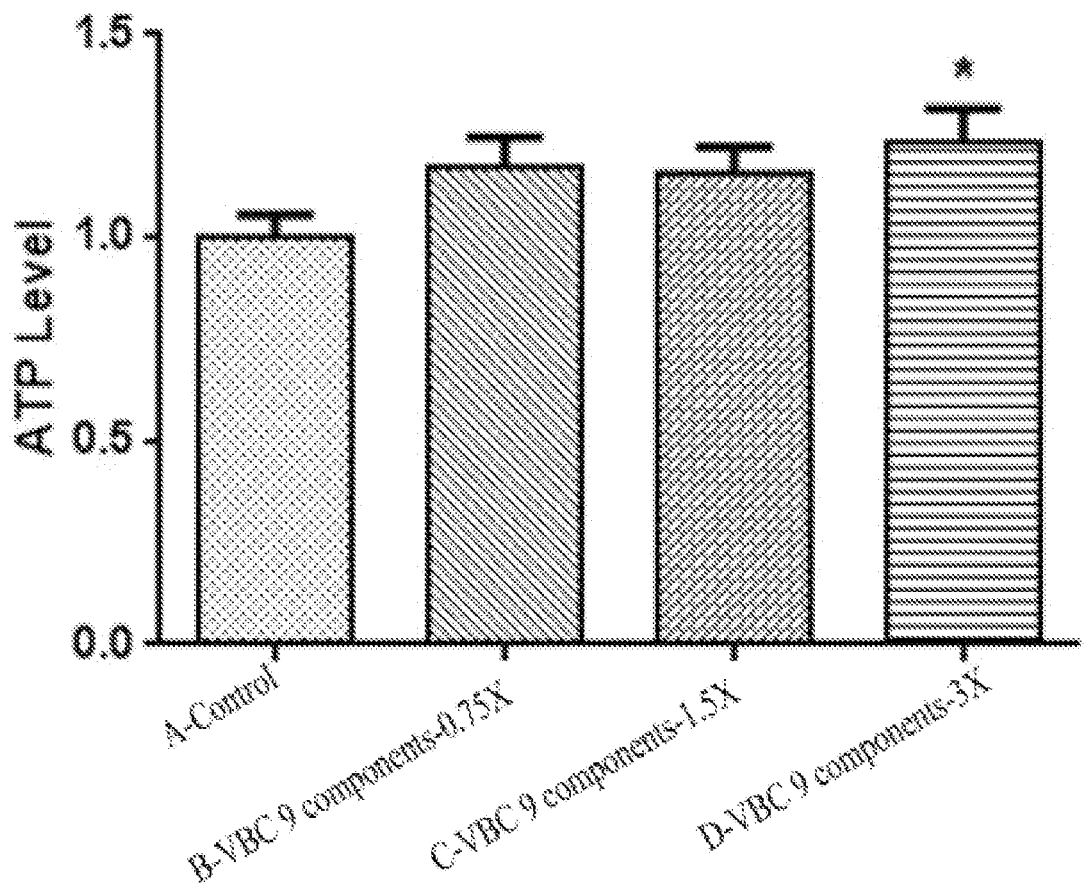
Figure 8. Effects of multiple doses of 9 components multivitamin BC on the ATP content of energy metabolism of small intestinal in mice.

COMPOSITION OF MULTIVITAMIN FOR STIMULATING GASTROINTESTINAL SYSTEM MOTILITY AND PREPARATION METHOD THEREFOR

This application is a U.S. National Stage Application under 35 U.S.C. § 371 of International Patent Application No. PCT/CN2019/083786, filed Apr. 23, 2019, which claims priority to CN provisional application No. 20/181,0400340.1, filed Apr. 28, 2018, CN provisional application No. 20/191,0099043.2, filed Jan. 31, 2019, and CN provisional application No. 20/191,0313858.6, filed Apr. 18, 2019, the disclosures of each of which are hereby incorporated by reference in their entirety.

FIELD OF THE INVENTION

The present invention relates to a composition of a multivitamin, vitamins B and C, and a preparation method therefor, and in particular, to a composition of a multivitamin, vitamins B and C for stimulating gastrointestinal system motility and a preparation method therefor. The composition is suitable for preventing and/or treating the statuses or diseases related to a lack of gastrointestinal motility.

BACKGROUND OF THE INVENTION

Nowadays, the pressure of people's life is generally increasing, the pace of life is accelerating, and the competition is fiercer day by day. More and more patients are suffering from gastrointestinal disorders or gastrointestinal discomfort. The pathogeny thereof is extensive, and the symptoms thereof are also different.

Gastrointestinal (GI) motility is a coordinated neuromuscular process that transports nutrients through the digestive system. Impaired motility of the gastrointestinal system can be involved in gastroesophageal reflux disease, gastroparesis (e.g., diabetic and postsurgical gastroparesis), irritable bowel syndrome (IBS), ileus, and constipation (e.g., functional or drug-induced constipation), and is one of the largest health care burdens of industrialized nations. In view of the above, a way to effectively stimulate motility of the gastrointestinal system is highly desirable and would be an advance in the art.

Functional dyspepsia and chronic gastritis often have such symptoms as abdominal fullness, upper abdominal pain, nausea, anorexia and so on. An important reason for this kind of symptoms is delayed gastric emptying caused by gastrointestinal motility disorders. And gastrointestinal motility disorders tend to cause IBS. Currently, drugs for treatment of gastrointestinal motility include metoclopramide, domperidone and itopride.

In the past, there were many kinds of drugs for treatment of gastrointestinal diseases, but few drugs have good curative effects and no side effects, and drugs or health care products with long-term health care effects as well as improving gastrointestinal function, promoting gastrointestinal motility and relieving gastrointestinal discomfort symptoms are even rare.

As mentioned above, (1) metoclopramide as a dopamine receptor blocking drug with strong central anti-vomiting and gastrointestinal tract excitement effects, can inhibit the relaxation of gastric smooth muscle, increase the response of gastrointestinal smooth muscle to cholinergic, accelerate gastric emptying, and increase the activity of the gastric antrum. In addition, the drug also has the function of stimulating the release of prolactin. The side effects of Metoclopramide commonly include lethargy, irritability, fatigue, and weakness. Moreover, high-dose or long-term use of the drug may block the dopamine receptor, showing the symptoms of Parkinson's disease. (2) Domperidone as a peripheral dopamine receptor antagonist can promote upper gastrointestinal peristalsis and tension recovery, facilitate gastric emptying, increase the movement of gastric antrum and duodenum, coordinate pyloric contraction, and enhance esophageal peristalsis and the tension of the lower esophageal sphincter. Because of its poor penetration into the blood brain barrier, domperidone almost has no antagonistic effect on the dopamine receptor in the brain. It is reported abroad that its high-dose intravenous injection may cause seizures (there is no this preparation in China). This drug, however, is a powerful prolactin-releasing drug which may cause menstrual disorders. (3) Itopride has dual effects of dopamine receptor blockade and acetylcholinesterase inhibition. It can enhance the movement of stomach and duodenum and facilitate gastric emptying by stimulating the release of endogenous acetylcholine and inhibiting the hydrolysis thereof. It also has a moderate anti-vomiting effect. The elderly or aged patients should use this drug with caution.

B vitamins are all water soluble, most of which are coenzymes, taking part in the in vivo metabolism of sugar, protein and fat. There are more than 12 kinds of vitamins in vitamin B group. Among which 9 kinds are recognized by the world unanimously and they are all water soluble. They stay in the body for only a few hours and must be supplemented daily. B vitamins are essential nutrient in all human tissues and they are very important for releasing energy from the food. They are all coenzymes which involved in the metabolism of sugar, protein and fat in the body. Therefore they are classified as a family.

All kinds of B vitamins must function at the same time, which is called vitamin B's fusion function. Intaking of a certain kind of vitamin B alone, the activity of the cell increases and then the demand for other vitamin B increases too, so the role of all kinds of vitamin B is complementary. It is called "barrel principle". Dr Roger Williams points out that all cells have exactly the same need for B vitamins.

The common members of the B vitamins family include B1, B2, B3, B5, B6, B7, B9, and B12. Their functions are described below.

Vitamin B1 (thiamine) can promote gastrointestinal peristalsis and increase appetite. Vitamin B1 can inhibit the activity of cholinesterase to hydrolyze acetylcholine. Lack of vitamin B1 may increase the activity of cholinesterase and accelerate the hydrolysis of acetylcholine. Acetylcholine is an important neurotransmitter and its deficiency can lead to nerve conduction disorders, especially affecting the nerve conduction at the gastrointestinal tract and gland, and lead to slow gastrointestinal peristalsis, abdominal distension, diminished digestive glandular secretion, and appetite decrease.

Vitamin B2 constitutes many important coenzymes in the flavoproteins. It can be converted into flavin mononucleotide (FMN) and flavin adenine dinucleotide (FAD), both of which are important coenzymes in the tissue respiration, function to transfer hydrogen in the enzyme system, and participate in the metabolism of sugar, protein and fat, and can maintain normal visual function. Furthermore, Vitamin B2 can activate Vitamin B6 and convert tryptophan into niacin, and may be related to maintaining the integrity of red blood cells. It can maintain and improve the health of epithelial tissue, such as the gastrointestinal mucosal tissue. When the human body lacks B2, especially in severe deficiency status, the mucosal layer of human body cavity will have problems that cause mucosal lesions, and this can enhance the carcinogenic effect of chemical carcinogens. Vitamin B2 can thus prevent cancer.

Vitamin B3 (niacin) constitutes a coenzyme of dehydrogenase in the body. Vitamin B3, as the most requisite amount of B vitamins of the human body, not only keeps health of the digestive system, but also alleviates gastrointestinal disorders. Niacin is converted into nicotinamide in the human body. Nicotinamide is a component of coenzyme I and coenzyme II and participates in the in vivo lipid metabolism, oxidation process of tissue respiration, and the anaerobic decomposition of carbohydrates. It can keep the health of the digestive system, relieve gastrointestinal disorders, and effectively relieve the symptoms of constipation. Its deficiency can lead to angular cheilitis, glossitis, diarrhea, and so on. Diarrhea is a typical symptom of this disease. Constipation often occurs in its early days. Then it is often accompanied by diarrhea because of enteritis and the atrophy of the intestinal wall, digestive gland, intestinal wall and mucosa, and intestinal villus. The stool is watery or pasty, with large quantities and a lot of stink and sometimes with blood. Tenesmus may happen when the lesion is near the anus. Diarrhea is often severe and refractory and can be combined with absorption disorders.

Vitamin B5 (pantothenic acid) has an active form of coenzyme A, is an acyl carrier in vivo, and participates in the metabolism of sugar, fat, and protein. They work synergistically to regulate metabolism, maintain skin and muscle health, enhance the functions of the immune system and nervous system, and promote cell growth and division (including promotion of production of red blood cells and prevention of anemia). The lack of vitamin B5 may lead to the symptoms including anepithymia, dyspepsia, and being susceptible to duodenal ulcer.

Vitamin B6 comprises pyridoxine, pyridoxal and pyridoxamine, which can be transformed to one another. It can react with ATP in vivo via an enzyme and then be transformed into a coenzyme of a variety of enzymes having physiological activity, thereby participating in various metabolic functions of amino acids and fats. Combined with vitamin B1, it has a strong analgesic effect. Vitamin B12 can enhance the analgesic effect by the combination of the above two, and relieve the pain caused by peripheral nerve disease and spinal cord disease. Studies have reported that the intravenous drip of vitamin B6 mixed with azithromycin can reduce side effects of azithromycin on the gastrointestinal tract. Its main targets are blood, muscle, nerves, skin, etc. Its functions are the synthesis of antibodies, production of gastric acid in the digestive system, utilization of fat and protein (which should be supplemented especially on a diet), and the maintenance of the sodium/potassium balance (stabilization of the nervous system). Lack of vitamin B6 damages cells and affect humoral immunity. Feeding of vitamin B6 can improve immunity, reduce carcinogens in the body, and has a certain anticancer effect.

Vitamin B7, also known as vitamin H, biotin, and coenzyme R, is involved in the metabolism of fatty acids and carbohydrates in the body, promoting protein synthesis. It also involved in the metabolism of vitamin B12, folic acid, and pantothenic acid. It can promote urea synthesis and excretion, enhance the body's immune response and resistance to infection, stabilize the lysosomal membrane of normal tissues, maintain the body's humoral immunity and cellular immunity, affect the secretion of a series of cytokines, improve the body's immune function, and reduce the symptoms of perianal eczema and itching. The biotin side chain carboxyl group can be linked to the lysine residues of the enzyme via an amide bond. Biotin is a carboxyl carrier and is also involved in the metabolism of vitamin B12, folic acid, and pantothenic acid.

Vitamin B9 (folic acid) belongs to water-soluble B vitamins consisting of pteridine, p-aminobenzoic acid, and glutamic acid residues. The drug is absorbed by the intestinal tract and then passes through the portal vein into the liver, where it is converted into an active tetrahydrofolic acid under the action of the dihydrofolate reductase. Tetrahydrofolic acid is the carrier of "one carbon group" in the body. The "one carbon group" can be linked to the tetrahydrofolic acid at its 5 or 10-position carbon atom, and is mainly involved in the synthesis and transformation of purine nucleotides and pyrimidine nucleotides. The methyl group required for conversion of uracil nucleotides to thymidine nucleotides is derived from the methylene group provided by tetrahydrofolic acid bearing a "one carbon group". As a result, folic acid deficiency can result in a "one carbon group" transfer barrier, and a difficult synthesis of thymidine nucleotide, thereby affecting DNA synthesis and slowing down the rate of cell division, that is, the cell cycle will only stay in the G1 phase and the S and G2 phases will be relatively prolonged. The above changes will affect not only hematopoietic cells (causing the megaloblastic anemia) but also the somatic cells (especially the digestive tract mucosal cells). Folic acid deficiency can lead to B1 absorption disorders. The health benefits of folic acid for women are widely noted in the medical community, and pregnant and lactating women should be supplemented with folic acid. Besides, it can be used to prevent rectal cancer and heart disease. It has also been found to prevent free radicals from destroying chromosomes. Humans with deficient folic acid may suffer from megaloblastic anemia and leukopema.

Deoxyadenosine cobalamin is the main existing form of vitamin B12 in the body and is a cobalt-containing red compound that is active only after it is converted to methylcobalamin and coenzyme B12. Vitamin B12 and folic acid play an important role in DNA synthesis. In addition, vitamin B12 also plays an important role in the maturation of red blood cells and in the normal maintenance of the nervous system. It is often associated with the role of folic acid. Folic acid has multiple coenzyme forms in the cell, and some studies have suggested that folic acid can intervene in the occurrence of gastrointestinal cancer and that folic acid can treat atrophic gastritis and improve gastric mucosal pathology.

Choline bitartrate has the effect of promoting the transformation of phospholipids and accelerating the operation of fat, and has a cholagogic effect; inositol can promote cell metabolism, promote development, and increase appetite. P-aminobenzoic acid (PABA) is actually a component of folic acid and it functions as a coenzyme in the body. PABA works with folic acid to promote protein metabolism and blood cell production.

Vitamin C, also known as ascorbic acid, is one of antioxidant vitamins. It participates in hydroxylation reaction in the body and is required for the formation of bones, teeth, and the interstitial adhesions in connective tissues and non-epithelial tissues. It can maintain the normal function of the teeth, bones, and blood vessels, and increase resistance to diseases. It is reported that vitamin C is deficient at different levels in various populations. When the body has some small problems, people should promptly be supplemented with vitamins and minerals to improve nutrition deficiencies, especially the elderly should pay more attention. Vitamins have a preventive effect on many diseases, many diseases may be more or less related to the lack of vitamin C, and vitamin C can also be combined with many other drugs to treat some diseases. Vitamin C is an antioxidant that protects the body from the threat of free redicals. Vitamin C is also a coenzyme. Many studies have shown that vitamin C can block the synthesis of carcinogenic N-nitroso compounds, prevent the formation of carcinogenic ammonium nitrate in the salted, pickled, and smoked foods containing nitrite (bacon, sausage, and so on), and prevent cancer, especially it has a better preventive effect on rectal cancer and colon cancer. At the same time, it has the effect of softening the blood vessels of the anus and increasing the elasticity of the anus. VC is easily damaged by heat or oxidants, especially light, trace heavy metals, and fluorescent substances can promote its oxidation, which makes VC be greatly restricted in application. Therefore, derivatives of vitamin C, including metal salts of VC, esters generated by VC with various acids, and compounds of VC and carbohydrates, etc., not only can get rid of the instability nature of VC, but also can better exert the physiological function of VC. These derivatives include vitamin C (L-ascorbic acid), Sodium ascorbate (L-sodium ascorbate), magnesium ascorbyl phosphate, L-Ascorbate-polyphosphate, ascorbyl palmitate, ascorbin stearate, vitamin C and glucose compound, etc.

From the perspective of mechanism of action, vitamin B is an important coenzyme involved in energy metabolism of human body, and vitamin C can promote the body's absorption of members of B vitamins. Multivitamin B C is used to improve the energy metabolism of the human body and provide more energy for the gastrointestinal tract to improve the functional dyspepsia caused by inadequate gastrointestinal motility. The mechanism for the increase in energy metabolism includes assisting carbohydrates and fat in releasing energy, decomposing amino acids, and transporting nutrient-containing oxygen and energy throughout the body. These compounds are found in natural foods and are generally not synthesized in the body or insufficient to meet the needs. Generally water-soluble vitamins stay in the body for no more than 24 hours. The deficiency of B vitamins will affect the metabolism of sugar, fat and protein. If not be supplemented in time, it is harmful to the growth and development of the body. In addition, the damage to bone, nerve and corneal tissue caused by the lack of vitamins can only be prevented from further damage even if sufficient supplements are taken in the future and this damage can never be reversed. Therefore, the water-soluble vitamins must be taken daily in order to keep healthy.

In order to supplement these nutrients comprehensively, a variety of vitamins are usually added at the same time as raw materials to produce products, such as multi-dimensional tablets, multi-dimensional granulations. The advantage of this kind of product is that it can supplement multivitamin at the same time by taking it once. It is favored by more and more consumers for its convenience. Multivitamin BC will be likely to become a new drug or health food with higher safety for promoting the motility of gastrointestinal system. The application shows evidence to prove the ability of vitamin B and vitamin C to promote the motility of the gastrointestinal system, especially the therapeutic and regulatory effect of vitamin B and vitamin C on motility disorders of the gastrointestinal system in pathological state. Due to the large number of family members of B vitamins and their interdependent relationship, component and dose selection and concomitant of the B vitamins are very important for preparation of drugs or health food for the treatment or regulation of motility disorders of the gastrointestinal system.

At present, the process of making multi-vitamin tablets or multi-vitamin mineral particles is to mix a variety of vitamins, a variety of mineral raw materials and excipients together, After mixture, granulation and desiccation, multidimensional particles are made, or then pressed into tablet. In addition, multi-vitamins, other raw materials, auxiliary materials are mixed with soybean oil, and then suspending agents are added to make multi-vitamin soft capsule.

However, the products made by the above processes have deficiencies. Due to their chemical properties, some vitamins will react with other raw and auxiliary materials, thus reducing the content of vitamins and thereby reducing the product efficacy.

DISCLOSURE OF THE INVENTION

A. Summary of the Invention

The present invention relates to a method of stimulating the motility of the gastrointestinal system in a subject in need thereof, wherein said subject suffers from diseases (i.e., disorders, conditions, symptoms, or drug- or surgery-induced dysfunction) of the gastrointestinal system. The method comprises administering to a subject in need thereof a therapeutically effective amount of a composition comprising B vitamins and C vitamins. The vitamins referred to in this invention comprise their corresponding analogues or derivatives, for example, vitamin B1 means thiamine, analogs or derivatives thereof, vitamin B2 denotes riboflavin, analogs or derivatives thereof; vitamin B3 refers to nicotinic acid, analogs or derivatives thereof, niacin or niacinamide is commonly used; vitamin B5 means pantothenic acid, analogs or derivatives thereof, calcium pantothenate or sodium pantothenate are commonly used; vitamin B6 means pyridoxine, analogs or derivatives thereof; vitamin B7 is biotin, analogues or derivatives thereof; vitamin B9 means folic acid, analogs or derivatives thereof; vitamin B12 means cyanocobalamine, analogs or derivatives thereof; vitamin C means ascorbic acid, analogs or derivatives thereof; and so on. A composition comprising B vitamins and C vitamins provided by the invention for preventing and/or treating conditions or diseases associated with insufficient gastrointestinal system motility. wherein the combination of multivitamins BC comprising B vitamins, analogues or derivatives, and C vitamins, analogues or derivatives. wherein the multivitamins BC thereof are selected from vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is any combination of eight components comprising vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin C. In one preferred embodiment, the composition comprising B vitamins and C vitamins is a composition comprising vitamin B1, vitamin B2, vitamin B3, vitamin B5, vitamin B6, vitamin B7, vitamin B12, and vitamin C. In one preferred embodiment, the composition comprising B vitamins and C vitamins is a composition comprising vitamin B1, vitamin B2, vitamin B3, vitamin B5, vitamin B6, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin B12. In one more preferred embodiment, the composition comprising B vitamins and C vitamins is a composition comprising vitamin B1, vitamin B2, vitamin B3, vitamin B5, vitamin B6, vitamin B7, vitamin B9, vitamin 12, and vitamin C. In one more preferred embodiment, the composition comprising B vitamins and C vitamins are vitamin B1, vitamin B2, vitamin B3, vitamin B5, vitamin B6, vitamin B7, vitamin B9, vitamin 12, and vitamin C.

In another aspect, this invention provides a composition comprising an effective amount of a combination of B vitamins and C vitamins, and a pharmaceutically acceptable carrier. This composition comprising an effective amount of a combination of vitamin B1, vitamin B2, vitamin B3, vitamin B5, vitamin B6, vitamin B7, vitamin B9, vitamin 12, vitamin C, and a pharmaceutically acceptable carrier. In one preferred embodiment, the composition comprises any combination of eight components of vitamin B1, vitamin B2, vitamin B3, vitamin B5, vitamin B6, vitamin B7, vitamin B9, vitamin 12, vitamin C, and a pharmaceutically acceptable carrier. In one preferred embodiment, the composition comprises an effective amount of vitamin B2, vitamin B3, vitamin B5, vitamin B6, vitamin B7, vitamin B9, vitamin B12, vitamin C, and a pharmaceutically acceptable carrier. In one preferred embodiment, the composition comprises an effective amount of vitamin B1, vitamin B3, vitamin B5, vitamin B6, vitamin B7, vitamin B9, vitamin B12, vitamin C, and a pharmaceutically acceptable carrier. In one preferred embodiment, the composition comprises an effective amount of vitamin B1, vitamin B2, vitamin B5, vitamin B6, vitamin B7, vitamin B9, vitamin B12, vitamin C, and a pharmaceutically acceptable carrier. In one preferred embodiment, the composition comprises an effective amount of vitamin B1, vitamin B2, vitamin B3, vitamin B6, vitamin B7, vitamin B9, vitamin B12, vitamin C, and a pharmaceutically acceptable carrier. In one preferred embodiment, the composition comprises an effective amount of vitamin B1, vitamin B2, vitamin B3, vitamin B5, vitamin B7, vitamin B9, vitamin B12, vitamin C, and a pharmaceutically acceptable carrier. In one preferred embodiment, the composition comprises an effective amount of vitamin B1, vitamin B2, vitamin B3, vitamin B5, vitamin B6, vitamin B7, vitamin B9, vitamin C, and a pharmaceutically acceptable carrier. In one preferred embodiment, the composition comprises an effective amount of vitamin B1, vitamin B2, vitamin B3, vitamin B5, vitamin B6, vitamin B7, vitamin B12, vitamin C, and a pharmaceutically acceptable carrier. In one preferred embodiment, the composition comprises an effective amount of vitamin B1, vitamin B2, vitamin B3, vitamin B5, vitamin B6, vitamin B9, vitamin B12, vitamin C, and a pharmaceutically acceptable carrier. In one preferred embodiment, the composition comprises an effective amount of vitamin B1, vitamin B2, vitamin B3, vitamin B5, vitamin B6, vitamin B7, vitamin B9, vitamin B12, and a pharmaceutically acceptable carrier. In one more preferred embodiment, the composition comprises vitamin B1, vitamin B2, vitamin B3, vitamin B5, vitamin B6, vitamin B7, vitamin B9, vitamin 12, vitamin C, and a pharmaceutically acceptable carrier.

In yet another aspect, the present invention relates to a composition comprising an effective amount of a combination of B vitamins and C vitamins, and an effective amount of drugs for treating and/or preventing gastrointestinal diseases. The composition comprises an effective amount of a combination of vitamin B1, vitamin B2, vitamin B3, vitamin B5, vitamin B6, vitamin B7, vitamin B9, vitamin 12, vitamin C, and an effective amount of drugs for treating and/or preventing gastrointestinal diseases. In one preferred embodiment, the composition comprises any combination of eight components of vitamin B1, vitamin B2, vitamin B3, vitamin B5, vitamin B6, vitamin B7, vitamin B9, vitamin 12, vitamin C, and an effective amount of drugs for treating and/or preventing gastrointestinal diseases. In one preferred embodiment, the composition comprises an effective amount of vitamin B2, vitamin B3, vitamin B5, vitamin B6, vitamin B7, vitamin B9, vitamin B12, vitamin C, and an effective amount of drugs for treating and/or preventing gastrointestinal diseases. In one preferred embodiment, the composition comprises an effective amount of vitamin B1, vitamin B3, vitamin B5, vitamin B6, vitamin B7, vitamin B9, vitamin B12, vitamin C, and an effective amount of drugs for treating and/or preventing gastrointestinal diseases. In one preferred embodiment, the composition comprises an effective amount of vitamin B1, vitamin B2, vitamin B5, vitamin B6, vitamin B7, vitamin B9, vitamin B12, vitamin C, and an effective amount of drugs for treating and/or preventing gastrointestinal diseases. In one preferred embodiment, the composition comprises an effective amount of vitamin B1, vitamin B2, vitamin B3, vitamin B6, vitamin B7, vitamin B9, vitamin B12, vitamin C, and an effective amount of drugs for treating and/or preventing gastrointestinal diseases. In one preferred embodiment, the composition comprises an effective amount of vitamin B1, vitamin B2, vitamin B3, vitamin B5, vitamin B7, vitamin B9, vitamin B12, vitamin C, and an effective amount of drugs for treating and/or preventing gastrointestinal diseases. In one preferred embodiment, the composition comprises an effective amount of vitamin B1, vitamin B2, vitamin B3, vitamin B5, vitamin B6, vitamin B7, vitamin B9, vitamin C, and an effective amount of drugs for treating and/or preventing gastrointestinal diseases. In one preferred embodiment, the composition comprises an effective amount of vitamin B1, vitamin B2, vitamin B3, vitamin B5, vitamin B6, vitamin B7, vitamin B12, vitamin C, and an effective amount of drugs for treating and/or preventing gastrointestinal diseases. In one preferred embodiment, the composition comprises an effective amount of vitamin B1, vitamin B2, vitamin B3, vitamin B5, vitamin B6, vitamin B9, vitamin B12, vitamin C, and an effective amount of drugs for treating and/or preventing gastrointestinal diseases. In one preferred embodiment, the composition comprises an effective amount of vitamin B1, vitamin B2, vitamin B3, vitamin B5, vitamin B6, vitamin B7, vitamin B9, vitamin B12, and an effective amount of drugs for treating and/or preventing gastrointestinal diseases. In one more preferred embodiment, the composition comprises vitamin B1, vitamin B2, vitamin B3, vitamin B5, vitamin B6, vitamin B7, vitamin B9, vitamin 12, vitamin C, and an effective amount of drugs for treating and/or preventing gastrointestinal diseases.

Promotion of gastrointestinal motility is used in a method for the treatment of drug-induced gastrointestinal dysfunction (e.g., opioid-induced, such as morphine-induced intestinal dysfunction or constipation) in an object in need thereof. The method comprises administering a therapeutically effective amount of a combination of B vitamins and C vitamins. Said object can be using opioid substances or opioids for post-surgical pain control or chronic pain control. Examples of opioid substances and opioids include morphine, codeine, oxycodone, hydrocodone, methadone, fentanyl, and the combination thereof with an anti-inflammatory agent (such as acetaminophen or aspirin). Wherein the combination of multivitamins BC are selected from vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is any combination of eight components comprising vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin C. In one preferred embodiment, the composition comprising B vitamins and C vitamins is a composition comprising vitamin B1, vitamin B2, vitamin B3, vitamin B5, vitamin B6, vitamin B7, vitamin B12, and vitamin C. In one preferred embodiment, the composition comprising B vitamins and C vitamins is a composition comprising vitamin B1, vitamin B2, vitamin B3, vitamin B5, vitamin B6, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin B12. In one more preferred embodiment, the composition comprising B vitamins and C vitamins is a composition comprising vitamin B1, vitamin B2, vitamin B3, vitamin B5, vitamin B6, vitamin B7, vitamin B9, vitamin 12, and vitamin C.

The promotion of gastrointestinal motility can be used to treat gastroparesis in an object in need thereof by administering a therapeutically effective amount of a combination of B vitamins and C vitamins. Wherein the combination of multivitamins BC are selected from vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is any combination of eight components comprising vitamin B1, vitamin B2, vitamin B3, vitamin B5, vitamin B6, vitamin B7, vitamin B9, vitamin B12 and vitamin C. In one preferred embodiment, the composition comprising B vitamins and C vitamins is a composition comprising vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin C. In one preferred embodiment, the composition comprising B vitamins and C vitamins is a composition comprising vitamin B1, vitamin B2, vitamin B3, vitamin B5, vitamin B6, vitamin B7, vitamin B12, and vitamin C. In one preferred embodiment, the composition comprising B vitamins and C vitamins is a composition comprising vitamin B1, vitamin B2, vitamin B3, vitamin B5, vitamin B6, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin B12. In one more preferred embodiment, the composition comprising B vitamins and C vitamins is a composition comprising vitamin B1, vitamin B2, vitamin B3, vitamin B5, vitamin B6, vitamin B7, vitamin B9, vitamin 12, and vitamin C.

In another embodiment, the promotion of gastrointestinal motility is used in a method for the treatment of a gastro esophageal reflux disease (GERD) in an object in need thereof. The method comprises administering a therapeutically effective amount of a combination of B vitamins and C vitamins. Wherein the combination of multivitamins BC are selected from vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is any combination of eight components comprising vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin C. In one preferred embodiment, the composition comprising B vitamins and C vitamins is a composition comprising vitamin B1, vitamin B2, vitamin B3, vitamin B5, vitamin B6, vitamin B7, vitamin B12, and vitamin C. In one preferred embodiment, the composition comprising B vitamins and C vitamins is a composition comprising vitamin B1, vitamin B2, vitamin B3, vitamin B5, vitamin B6, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin B12. In one more preferred embodiment, the composition comprising B vitamins and C vitamins is a composition comprising vitamin B1, vitamin B2, vitamin B3, vitamin B5, vitamin B6, vitamin B7, vitamin B9, vitamin 12, and vitamin C. In a specific embodiment, said gastro esophageal reflux disease is nighttime gastro esophageal reflux disease.

The invention also provides a method of promoting gastrointestinal motility to treat the irritable bowel syndrome (IBS) in an object in need thereof by administering a therapeutically effective amount of a combination of B vitamins and C vitamins. Wherein the combination of multivitamins BC are selected from vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is any combination of eight components comprising vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin C. In one preferred embodiment, the composition comprising B vitamins and C vitamins is a composition comprising vitamin B1, vitamin B2, vitamin B3, vitamin B5, vitamin B6, vitamin B7, vitamin B12, and vitamin C. In one preferred embodiment, the composition comprising B vitamins and C vitamins is a composition comprising vitamin B1, vitamin B2, vitamin B3, vitamin B5, vitamin B6, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin B12. In one more preferred embodiment, the composition comprising B vitamins and C vitamins is a composition comprising vitamin B1, vitamin B2, vitamin B3, vitamin B5, vitamin B6, vitamin B7, vitamin B9, vitamin 12, and vitamin C.

The invention also provides a method for treating constipation by promoting gastrointestinal motility in an object in need thereof by administering a therapeutically effective amount of a combination of B vitamins and C vitamins. The constipation comprises functional constipation (caused by bad habits, dietary habits, senility, and other non-organic pathology) and drug-induced constipation. Wherein the combination of multivitamins BC are selected from vitamin B1; vitamin B2, vitamin B3, vitamin B5, vitamin B6, vitamin B7, vitamin B9, vitamin B12, and vitamin C. In one preferred embodiment, the composition comprising B vitamins and C vitamins is any combination of eight components comprising vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin C. In one preferred embodiment, the composition comprising B vitamins and C vitamins is a composition comprising vitamin B1, vitamin B2, vitamin B3, vitamin B5, vitamin B6, vitamin B7, vitamin B12, and vitamin C. In one preferred embodiment, the composition comprising B vitamins and C vitamins is a composition comprising vitamin B1, vitamin B2, vitamin B3, vitamin B5, vitamin B6, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin B12. In one more preferred embodiment, the composition comprising B vitamins and C vitamins is a composition comprising vitamin B1, vitamin B2, vitamin B3, vitamin B5, vitamin B6, vitamin B7, vitamin B9, vitamin 12, and vitamin C.

In one embodiment, the promotion of gastrointestinal motility is used in a method for treatment of gastrointestinal dysfunction caused by or associated with surgery (such as the slowdown of intestinal peristalsis after operation) in an object in need thereof, the method comprising administering a therapeutically effective amount of a combination of B vitamins and C vitamins. Wherein the combination of multivitamins BC are selected from vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is any combination of eight components comprising vitamin B1, vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B2, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B3, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B5, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B6, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B7, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin C. In one preferred embodiment, the composition comprising B vitamins and C vitamins is a composition comprising vitamin B1, vitamin B2, vitamin B3, vitamin B5, vitamin B6, vitamin B7, vitamin B12, and vitamin C. In one preferred embodiment, the composition comprising B vitamins and C vitamins is a composition comprising vitamin B1, vitamin B2, vitamin B3, vitamin B5, vitamin B6, vitamin B9, vitamin B12, and vitamin C. In one preferred embodiment, the composition comprising B vitamins and C vitamins is a composition comprising vitamin B1, vitamin B2, vitamin B3, vitamin B5, vitamin B6, vitamin B7, vitamin B9, and vitamin B12. In one more preferred embodiment, the composition comprising B vitamins and C vitamins is a composition comprising vitamin B1, vitamin B2, vitamin B3, vitamin B5, vitamin B6, vitamin B7, vitamin B9, vitamin 12, and vitamin C.

The components of the preferred embodiment are selected from vitamin B1, vitamin B2, vitamin B3, vitamin B5, vitamin B6, vitamin B7, vitamin B9, vitamin B12, and vitamin C. The components of the preferred embodiment are selected from any combination of eight components comprising vitamin B1, vitamin B2, vitamin B3, vitamin B5, vitamin B6, vitamin B7, vitamin B9, vitamin B12, and vitamin C. A preferred composition comprises vitamin B2, vitamin B3, vitamin B5, vitamin B6, vitamin B7, vita min B9, vitamin B12, and vitamin C. A preferred composition comprises vitamin B1, vitamin B3, vitamin B5, vitamin B6, vitamin B7, vitamin B9, vitamin B12, and vitamin C. A preferred composition comprises vitamin B1, vitamin B2, vitamin B5, vitamin B6, vitamin B7, vitamin B9, vitamin B12, and vitamin C. A preferred composition comprises vitamin B1, vitamin B2, vitamin B3, vitamin B6, vitamin B7, vitamin B9, vitamin B12, and vitamin C. A preferred composition comprises vitamin B1, vitamin B2, vitamin B3, vitamin B5, vitamin B7, vitamin B9, vitamin B12, and vitamin C. A preferred composition comprises vitamin B1, vitamin B2, vitamin B3, vitamin B5, vitamin B6, vitamin B7, vitamin B9, and vitamin C. A preferred composition comprises vitamin B1, vitamin B2, vitamin B3, vitamin B5, vitamin B6, vitamin B7, vitamin B12, and vitamin C. A preferred composition comprises vitamin B1, vitamin B2, vitamin B3, vitamin B5, vitamin B6, vitamin B9, vitamin B12, and vitamin C. A preferred composition comprises vitamin B1, vitamin B2, vitamin B3, vitamin B5, vitamin B6, vitamin B7, vitamin B12, and vitamin C. A preferred composition comprises vitamin B1, vitamin B2, vitamin B3, vitamin B5, vitamin B6, vitamin B9, vitamin B12, and vitamin C. A more preferred composition comprises vitamin B1, vitamin B2, vitamin B3, vitamin B5, vitamin B6, vitamin B7, vitamin B9, vitamin 12, and vitamin C.

The dosage form of the composition comprising B vitamins and C vitamins of the present invention can be, but not limited to chewable tablet, In the present invention, various conventional auxiliary materials auxiliary materials required for preparing different dosage forms can also be added to the composition, such as disintegrants, lubricants, adhesive, antioxidants, complexing agents, and other pharmaceutical carriers to prepare commonly used oral dosage forms by conventional preparation methods, such as dispersible tablets, granules, capsules, oral liquids, and other dosage forms. In particular, the purpose of this invention is to avoid the interaction between multiple active components of vitamin BC compositions after contaction to maintain good stability. The multivitamin BC product of the present invention can be composed of one or more active components preparations respectively.

The weight ratio of each component for the composition comprising B vitamins and C vitamins in the present invention can have a plurality of selections, and all of them have corresponding motility promotion effects on the gastrointestinal system. In certain embodiments, it can include the following components based on weight ratio: 5-15 parts of vitamin B1, 5-15 parts of vitamin B2, 5-25 parts of vitamin B3, 10-110 parts of vitamin B5, 5-15 parts of vitamin B6, 0.01-0.1 parts of vitamin B7, 5-500 parts of vitamin C, 0.01-0.1 parts of vitamin B12, and 0.01-0.1 parts of vitamin B9. In one preferred embodiment, the composition comprising B vitamins and C vitamins is any combination of eight components based on weight ratio: 10 parts of vitamin B1, 5 parts of vitamin B2, 10 parts of vitamin B3, 10 parts of vitamin B5, 10 parts of vitamin B6, 0.01 parts of vitamin B7, 15 parts of vitamin C, 0.04 parts of vitamin B9, and 0.01 parts of vitamin B12. In one preferred embodiment, the multivitamins BC composition comprises the following components based on weight ratio: 10 parts of vitamin B1, 10 parts of vitamin B3, 10 parts of vitamin B5, 10 parts of vitamin B6, 0.01 parts of vitamin B7, 15 parts of vitamin C, 0.04 parts of vitamin B9, and 0.01 parts of vitamin B12. In one preferred embodiment, the multivitamins BC composition comprises the following components based on weight ratio: 5 parts of vitamin B2, 10 parts of vitamin B3, 10 parts of vitamin B5, 10 parts of vitamin B6, 0.01 parts of vitamin B7, 15 parts of vitamin C, 0.04 parts of vitamin B9, and 0.01 parts of vitamin B12. In one preferred embodiment, the multivitamins BC composition comprises the following components based on weight ratio: 10 parts of vitamin B1, 5 parts of vitamin B2, 10 parts of vitamin B5, 10 parts of vitamin B6, 0.01 parts of vitamin B7, 15 parts of vitamin C, 0.04 parts of vitamin B9, and 0.01 parts of vitamin B12. In one preferred embodiment, the multivitamins BC composition comprises the following components based on weight ratio: 10 parts of vitamin B1, 5 parts of vitamin B2, 10 parts of vitamin B3, 10 parts of vitamin B6, 0.01 parts of vitamin B7, 15 parts of vitamin C, 0.04 parts of vitamin B9, and 0.01 parts of vitamin B12. In one preferred embodiment, the multivitamins BC composition comprises the following components based on weight ratio: 10 parts of vitamin B1, 5 parts of vitamin B2, 10 parts of vitamin B3, 10 parts of vitamin B5, 0.01 parts of vitamin B7, 15 parts of vitamin C, 0.04 parts of vitamin B9, and 0.01 parts of vitamin B12. In one preferred embodiment, the multivitamins BC composition comprises the following components based on weight ratio: 10 parts of vitamin B1, 5 parts of vitamin B2, 10 parts of vitamin B3, 10 parts of vitamin B5, 10 parts of vitamin B6, 15 parts of vitamin C, 0.04 parts of vitamin B9, and 0.01 parts of vitamin B12. In one preferred embodiment, the multivitamins BC composition comprises the following components based on weight ratio: 10 parts of vitamin B1, 5 parts of vitamin B2, 10 parts of vitamin B3, 10 parts of vitamin B5, 10 parts of vitamin B6, 0.01 parts of vitamin B7, 0.04 parts of vitamin B9, and 0.01 parts of vitamin B12. In one preferred embodiment, the multivitamins BC composition comprises the following components based on weight ratio: 10 parts of vitamin B1, 5 parts of vitamin B2, 10 parts of vitamin B3, 10 parts of vitamin B5, 10 parts of vitamin B6, 0.01 parts of vitamin B7, 15 parts of vitamin C, and 0.01 parts of vitamin B12. In one preferred embodiment, the multivitamins BC composition comprises the following components based on weight ratio: 10 parts of vitamin B1, 5 parts of vitamin B2, 10 parts of vitamin B3, 10 parts of vitamin B5, 10 parts of vitamin B6, 0.01 parts of vitamin B7, 15 parts of vitamin C, and 0.04 parts of vitamin B9. In one preferred embodiment, the multivitamins BC composition comprises the following components based on weight ratio: 10 parts of vitamin B1, 5 parts of vitamin B2, 10 parts of vitamin B3, 10 parts of vitamin B5, 10 parts of vitamin B6, 0.01 parts of vitamin B7, 15 parts of vitamin C, 0.04 parts of vitamin B9, and 0.01 parts of vitamin B12. In one preferred embodiment, the multivitamins BC composition are the following components based on weight ratio: 10 parts of vitamin B1, 5 parts of vitamin B2, 10 parts of vitamin B3, 10 parts of vitamin B5, 10 parts of vitamin B6, 0.01 parts of vitamin B7, 15 parts of vitamin C, 0.04 parts of vitamin B9, and 0.01 parts of vitamin B12.

For this reason, the purpose of the present invention is to provide a kind of compound vitamin B and C combination product (multivitamin BC products), as well as provide a preparation method of multivitamin BC product. The product has high bioavailability. It is efficent to avoid the interaction between multiple active components of vitamin BC composition after contaction, and the product maintain good stability. The active components of this multivitamin BC product include one or more of vitamin B1, vitamin B2, vitamin B3, vitamin B6, vitamin B9, vitamin B12, vitamin C, vitamin B5, vitamin B7 and other vitamins. The compound multivitamin BC product of the invention contains three kinds of active components, among them the first active composition contains one or more of vitamin B1, vitamin B2, vitamin B3, vitamin B6, vitamin B9, and vitamin B12. The second active composition contains one or more of vitamin C, vitamin B5, the third active composition contains vitamin B7 or other vitamins. In one preferred embodiment, the first active composition contains vitamin B1, vitamin B2, vitamin B3, vitamin B6, vitamin B9 and vitamin B12, the second active composition contains vitamin C and vitamin B5, and the third active composition contains vitamin B7. In another embodiment, the first active composition are vitamin B1, vitamin B2, vitamin B3, vitamin B6, vitamin B9 and vitamin B12, the second active composition are vitamin C and vitamin B5, and the third active composition is vitamin B7. These three active compositions can be combined into their own preparation forms, and then a variety of technical solutions can be used to make a multivitamin BC product. These three active compositions can also be made into granulations, and then a variety of technical solutions can be used to make multivitamin BC products. In one preferred embodiment, the three active compositions are separately made into granulations and then mixed into tablets to make a compound vitamin BC single-layer tablet preparation product. In another preferred embodiment, the three active compositions are separately made into granulations, and each active composition is pressed into one layer to make a compound vitamin BC three-layer tablet product. In another preferred embodiment, after the three active compositions are combined into granulations, they are separately compressed and filled into capsules to make a multi-vitamin BC capsule product. In another preferred embodiment, after the three active compositions are combined into granulations, they are compressed into tablets separately, packaged separately or mixed and packaged in different bottles, bags or medicinal containers to make three multivitamin BC tablet products.

To achieve the above purposes, the invention provides the following technical scheme:

The multivitamin BC preparation product consists of a combination of three active compositios, which are separately made into granulations, compressed into tablets, and then packaged. The granular formula of each active composition contains one or more of active components, fillers, binders, disintegrants, glidants, lubricants and other auxiliary materials, different active components correspond to the same or different auxiliary materials. In one preferred embodiment, the three active compositions are combined into granulations, they are mixed and compressed to form a multivitamin BC monolayer tablet product. In another preferred embodiment, after the three active compositions are separately made into granulations, each active composition is pressed into one layer to make a multivitamin BC three-layer tablet product. In another preferred embodiment, after the three active compositions are combined into granulations, they are separately compressed and filled into capsules to make a multi-vitamin BC capsule product. In another preferred embodiment, after the three active compositions are combined into granulations, they are compressed into tablets separately, packaged separately or mixed and packaged in different bottles, bags or medicinal containers to make three multivitamin BC tablet products.

A multivitamin BC three-layer tablet preparation product, which is composed of a first layer, a second layer and a third layer. The second layer is located between the first layer and the third layer, and each layer is made of different granulations. The granulation formulation of each layer contains one or more active components and fillers, binders, disintegrants, glidants, lubricants and other auxiliary materials. Different active components correspond to the same or different auxiliary materials. The invention is made into three-layer tablet form after granulating multiple vitamins separately, so that different active components are in different auxiliary materials. It not only reduces the instability of active components caused by improper excipients, but also reduces the interaction between different active components, thus ensuring the stability of active components.

The active components of the first layer of the multivitamin BC three-layer tablet preparation product of the present invention include one or more of vitamin B1, vitamin B2, vitamin B3, vitamin B6, vitamin B9, vitamin B12, and one or more the auxiliary material includes microcrystalline cellulose, mannitol, sodium carboxymethyl starch, povidone K30, silicon dioxide, gelatin, and magnesium stearate. The active components of the first layer and auxiliary materials are mixed and then granulated to form the total mixed granulations of the first layer. The first layer of the total mixed granulations contains VB1V/B2V/B3V/B6 granulations, vitamin B9 granulations and VB12 granulations. Among them, preferably, 0.1-48 parts of vitamin B1, 0.1-25 parts of vitamin B2, 0.1-48 parts of vitamin B3, 1-50 parts of vitamin B6, 1-100 parts of microcrystalline cellulose, 1-100 parts of mannitol, 0.1-8.5 parts of sodium carboxymethyl cellulose, and 0.1-13 parts of povidone K30 are firstly prepared into VB1/VB2/VB3/VB6 granulations; 0.01-0.20 parts of vitamin B9, 0.1-22.5 parts of microcrystalline cellulose, 0.01-1.0 parts mannitol, 0.01-1.8 parts sodium carboxymethyl starch, 0.1-48.0 povidone K30 are prepared into vitamin B9 granulations; 0.001-0.05 parts vitamin B12, 0.1-50 parts microcrystalline cellulose, 0.001-0.33 parts silicon dioxide, 0.01-3.33 parts of gelatin are prepared into VB12 granulations. Among them, another preferred composition of active components are 48 parts of vitamin B1, 25 parts of vitamin B2, 48 parts of vitamin B3, 50 parts of vitamin B6, 0.20 parts of vitamin B9 and 0.05 parts of vitamin B12. After the above three kinds of granulations are uniformly mixed, the total mixed granulations of the first layer is obtained.

The active components of the second layer of the multivitamin BC three-layer tablet preparation product of the present invention include one or more of vitamin C and vitamin B5, and one or more of the auxiliary materials including microcrystalline cellulose, mannitol, sodium carboxymethyl starch, polyvinyl chloride, and ketone K30. The active components of the second layer and auxiliary materials are mixed and then granulated to form the total mixed granulations of the second layer. The total mixed granulations of the second layer tablet contain vitamin C granulations and vitamin B5 granulations. Preferably, in parts by weight, 1-75 parts of vitamin C, 1-50 parts of microcrystalline cellulose, 1-50 parts of mannitol, 0.1-3.8 parts of carboxymethyl starch, and 0.1-4.8 parts of povidone K30 are prepared into VC granulations. 1-52 parts of vitamin B5, 1-70 parts of microcrystalline cellulose, 1-70 parts of mannitol, 0.1-3.50 parts of sodium carboxymethyl starch, and 0.01-0.625 parts of povidone K30 are prepared into vitamins B5 granulations. Among them, another preferred active components are 75 parts of vitamin C and 52 parts of vitamin B5. The above two kinds of granulations are uniformly mixed to obtain the total mixed granulations of the second layer tablet.

The active components of the third layer of the multivitamin BC three-layer tablet preparation product of the present invention contain vitamin B7 or other vitamins, and one or more of the auxiliary materials including microcrystalline cellulose, mannitol, sodium carboxymethyl starch, povidone K30, and film coating materials. The active components of the third layer and auxiliary materials are mixed and then granulated to form the total mixed granulations of the third layer. The total mixed granulations of the third layer tablet contain vitamin B7 granulations. Preferably, in parts by weight, 0.001-0.05 parts of vitamin B7, 1-25 parts of microcrystalline cellulose, 0.1-25 parts of mannitol, 0.01-1.1 parts of sodium carboxymethyl starch, 0.01-2.0 parts of povidone K30, and film coating material 0.1-10.63 parts are prepared into vitamin B7 granulations. 1-80 parts of microcrystalline cellulose, 1-80 parts of mannitol, 0.1-4.25 parts of sodium carboxymethyl starch, and 0.1-8.5 parts of povidone K30 are prepared into blank granulations. Among them, another preferred active component is 0.05 parts of vitamin B7. Mix the above two kinds of granulations uniformly to obtain the total mixed granulations of the third layer tablet.

The active components and auxiliary materials of the first layer are mixed and then granulated to form the total mixed granulations of the first layer. The active components and auxiliary materials of the second layer are mixed and then granulated to form the total mixed granulations of the second layer. The active components and auxiliary materials are mixed and granulated to form the third layer of total mixed granulations. The total mixed granulations of the first layer, the second layer, and the third layer are compressed into a three-layer tablet. The specific process includes pouring the total mixed granulations of the first layer into the first material funnel of the three-layer tablet machine, operating the tablet machine, and adjusting the parameters to get the tablet weight reaches ±5% of the target tablet weight. Then the total mixed granulations of the second layer are poured into the second material funnel, adjusting the parameters to get the total weight (the first layer piece+the second layer piece) reaches ±5% of the target tablet weight. Finally the total mixed granulations of the third layer are poured into the third material funnel, adjusting the parameters to get the total weight (the first layer piece+the second layer piece+the third layer piece) reaches ±5% of the target piece weight. After the weight and hardness of the three-layer tablet are stabilized, the tablet is formally compressed, and then coated and packaged.

A kind of multivitamin BC capsule product, which is consist of three types of tablets packed in a hard shell capsule. Each type of tablet is made of different granulations. The granulation formula of each kind of tablet contains one or more active components, fillers, binders, disintegrants, glidants, lubricants, and other auxiliary materials. Different active components correspond to the same or different auxiliary materials. In the present invention, multiple vitamins are separately granulated and then compressed into three different types of tablets, so that different active components are in different auxiliary materials, which not only reduces the instability of active components caused by improper auxiliary materials, but also can reduces the interaction between multiple active components of vitamin BC composition after contaction, and then ensure the active components stability.

Among the first type of tablet in the capsule of the present invention, the active components contain one or more of vitamin B1, vitamin B2, vitamin B3, vitamin B6, vitamin B9, and vitamin B12, the auxiliary materials contains one or more of microcrystalline cellulose, mannitol, carboxymethyl starch sodium, lactose, povidone K30, silicon dioxide, gelatin, and magnesium stearate, etc. The first active components are mixed with the excipients and then granulated to form the total mixed granulations of the first type of tablet. There are granulations of VB1/VB2/VB3/VB6, vitamin B9 and vitamin B12 in the total mixed granulations of the first type of tablet. Preferably, 0.1-48 parts of vitamin B1, 0.1-25 parts of vitamin B2, 0.1-48 parts of vitamin B3, 1-50 parts of vitamin B6, 1-100 parts of microcrystalline cellulose, 1-100 parts of mannitol, 0.1-8.5 parts of sodium carboxymethyl cellulose, and 0.1-13 parts of polyvitone K30 are firstly prepared into VB1/VB2/VB3/VB6 granulations. Vitamin B9 granulations were prepared from 0.01-0.20 parts of vitamin B9, 0.1-22.5 parts of microcrystalline cellulose, 0.01-1.0 parts of mannitol, 0.01-1.8 parts of sodium carboxymethyl starch, and 0.1-48.0 parts of povidone K30. 0.001-0.05 parts of vitamin B12, 0.1-50 parts of microcrystalline cellulose, 0.001-0.33 parts of silicon dioxide, 0.01-3.33 parts of gelatin are prepared into VB12 granulations. wherein another preferred combination of active components is 48 parts of vitamin B1, 25 parts of vitamin B2, 48 parts of vitamin B3, 50 parts of vitamin B6, 0.20 parts of vitamin B9 and 0.05 parts of vitamin B12. The above three kinds of granulations are mixed uniformly and compressed to obtain the first type of tablet.

Among the second type of tablet in the capsule of the present invention, the active components contain one or more of vitamin C and vitamin B5, and the auxiliary material contains one or more of microcrystalline cellulose, mannitol, sodium carboxymethyl starch, and povidone K30. The second active component and auxiliary materials are mixed and then granulated to form the total mixed granulations of the second tablet. There are vitamin C granulations and vitamin B5 granulations in the total mixed granulations of the second type of tablet. Preferably, wherein in parts by weight, 1-75 parts of vitamin C, 1-50 parts of microcrystalline cellulose, 1-50 parts of mannitol, 0.1-3.8 parts of carboxymethyl starch, and 0.1-4.8 parts of povidone K30 are prepared into vitamin C granulations; 1-52 parts of vitamin B5, 1-70 parts of microcrystalline cellulose, 1-70 parts of mannitol, 0.1-3.50 parts of sodium carboxymethyl starch, and 0.01-0.625 parts of povidone K30 are prepared into vitamin B5 granulations. Wherein another preferred combination of active components is 75 parts of vitamin C and 52 parts of vitamin B5. The above two kinds of granulations are uniformly mixed and compressed to obtain the second type of tablet.

Among the third type of tablet in the capsule of the present invention, the active component contains vitamin B7 or other vitamins, and the auxiliary material contains one or more of microcrystalline cellulose, mannitol, sodium carboxymethyl starch, povidone K30, and the film coating materials. The third active component and auxiliary materials are mixed and then granulated to form the total mixed granulations of the third type of tablet. There are vitamin B7 granulations and blank granulations in the total mixed granulations of the third type of tablet. Preferably, in parts by weight, 0.001-0.05 parts of vitamin B7, 1-25 parts of microcrystalline cellulose, 0.1-25 parts of mannitol, 0.01-1.1 parts of sodium carboxymethyl starch, 0.01-2.0 parts of povidone K30, and 0.1-10.63 parts of film coating material are prepared into vitamin B7 granulations. 1-80 parts of microcrystalline cellulose, 1-80 parts of mannitol, 0.1-4.25 parts of sodium carboxymethyl starch, and 0.1-8.5 parts of povidone K30 are prepared into blank granulations. In another preferred active component is 0.05 parts of vitamin B7. The above two kinds of granulations are uniformly mixed and compressed to obtain the third type of tablet.

By using a capsule filling machine, three types of tablets are filled into the same capsule and then packaged. Preferably, 3 tablets of the first type of tablet, 2 tablets of the second type of tablet and 1 tablet of the third type of tablet (vitamin B7 tablet) are filled into the same capsule and then packaged.

A kind of multivitamin BC three-tablets preparation product, which is composed by three types of tablets. Each type of tablet is made of different granulations. The granulation formula of each tablet contains one or more active components, fillers, binders, disintegrants, glidants, lubricants, and other auxiliary materials. Different active components correspond to the same or different auxiliary materials. In the present invention, multiple vitamins are separately granulated and then compressed into three different tablets, so that different active components are in different auxiliary materials, which not only reduces the instability of active components caused by improper auxiliary materials, but also can reduces the interaction between multiple active components of vitamin BC composition after contact, and then ensure the active components stability.

The active components and auxiliary materials of the first type of tablet are mixed and then granulated to form the granulations of the first type of tablet. The active components and auxiliary materials of the second type of tablet are mixed and then granulated to form the granulations of the second type of tablet. The active components and auxiliary materials of the third type of tablet are mixed and then granulated to form the granulations of the third type of tablet. The mixed granulations of the three types of tablets are transferred to a rotary tablet press for pressing to obtain three different types of tablets and coated respectively. The three types of tablets are packaged separately or mixed and then packaged in different bottles, bags or medical containers.

Among the first type of tablet of the three types tablets of multivitamin BC product, the active components contain one or more of vitamin B1, vitamin B2, vitamin B3, vitamin B6, vitamin B9, and vitamin B12, the auxiliary materials contains one or more of microcrystalline cellulose, mannitol, carboxymethyl starch sodium, lactose, povidone K30, silicon dioxide, gelatin, and magnesium stearate, etc. The first active components are mixed with the excipients and then granulated to form the total mixed granulations of the first type of tablet. There are granulations of VB1/VB2/VB3/VB6, vitamin B9 and vitamin B12 in the total mixed granulations of the first type of tablet. Preferably, 0.1-48 parts of vitamin B1, 0.1-25 parts of vitamin B2, 0.1-48 parts of vitamin B3, 1-50 parts of vitamin B6, 1-100 parts of microcrystalline cellulose, 1-100 parts of mannitol, 0.1-8.5 parts of sodium carboxymethyl cellulose, and 0.1-13 parts of polyvitone K30 are firstly prepared into VB1/VB2/VB3/VB6 granulations. Vitamin B9 granulations were prepared from 0.01-0.20 parts of vitamin B9, 0.1-22.5 parts of microcrystalline cellulose, 0.01-1.0 parts of mannitol, 0.01-1.8 parts of sodium carboxymethyl starch, and 0.1-48.0 parts of povidone K30. 0.001-0.05 parts of vitamin B12, 0.1-50 parts of microcrystalline cellulose, 0.001-0.33 parts of silicon dioxide, 0.01-3.33 parts of gelatin are prepared into VB12 granulations. Another preferred combination of active components are 48 parts of vitamin B1, 25 parts of vitamin B2, 48 parts of vitamin B3, 50 parts of vitamin B6, 0.20 parts of vitamin B9 and 0.05 parts of vitamin B12. The above three kinds of granulations are mixed uniformly and compressed to obtain the first type of tablet.

Among the second type of tablet of the three types of tablets preparation products of multivitamin BC products, the active component contains one or more of vitamin C and vitamin B5, and the auxiliary materials contains one or more of microcrystalline cellulose, mannitol, sodium carboxymethyl starch, and povidone K30. The second active component and auxiliary materials are mixed and then granulated to form the total mixed granulations of the second type of tablet. There are vitamin C granulations and vitamin B5 granulations in the total mixed granulations of the second type of tablet. Preferably, wherein in parts by weight, 1-75 parts of vitamin C, 1-50 parts of microcrystalline cellulose, 1-50 parts of mannitol, 0.1-3.8 parts of carboxymethyl starch, and 0.1-4.8 parts of povidone K30 are prepared into vitamin C granulations; 1-52 parts of vitamin B5, 1-70 parts of microcrystalline cellulose, 1-70 parts of mannitol, 0.1-3.50 parts of sodium carboxymethyl starch, and 0.01-0.625 parts of povidone K30 are prepared into vitamin B5 granulations. Wherein another preferred combination of active components is 75 parts of vitamin C and 52 parts of vitamin B5. The above two kinds of granulations are uniformly mixed and compressed to obtain the second type of tablet.

Among the third type of tablet of the three types of tablets preparation products of multivitamin BC products, the active components contain vitamin B7 or other vitamins, and the auxiliary material contains one or more of microcrystalline cellulose, mannitol, sodium carboxymethyl starch, povidone K30, and the film coating materials. The third active component and auxiliary materials are mixed and then granulated to form the total mixed granulations of the third type of tablet. There are vitamin B7 granulations and blank granulations in the total mixed granulations of the third type of tablet. Preferably, in parts by weight, 0.001-0.05 parts of vitamin B7, 1-25 parts of microcrystalline cellulose, 0.1-25 parts of mannitol, 0.01-1.1 parts of sodium carboxymethyl starch, 0.01-2.0 parts of povidone K30, and 0.1-10.63 parts of film coating material are prepared into vitamin B7 granulations. 1-80 parts of microcrystalline cellulose, 1-80 parts of mannitol, 0.1-4.25 parts of sodium carboxymethyl starch, and 0.1-8.5 parts of povidone K30 are prepared into blank granulations. Another preferred active component is 0.05 parts of vitamin B7. The above-mentioned three types of tablets are separately packaged or mixed and packaged in different bottles, bags or medical containers to form the three types of tablets preparation product of multivitamin BC products.

B. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" mean "at least one" or "one or more" unless the context clearly dictates otherwise.

The term "part," particularly referring to a given quantity, refers to a quantity with a positive or negative deviation within 10%.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

As used herein, the term "B vitamins composition" includes all kinds of vitamin B or their corresponding analogues or derivatives, for example, vitamin B1 (thiamine), vitamin B2 (riboflavin), vitamin B3 (nicotinic acid), vitamin B5 (pantothenic acid), vitamin B6 and so on. Vitamins referred in the present invention include their corresponding analogues or derivatives, for example, vitamin B1 refers to thiamine or its analogues or derivatives; vitamin B2 refers to riboflavin or its analogues or derivatives; vitamin B3 refers to niacin or its analogues or derivatives, such as niacin, nicotinamide, etc.; vitamin B5 refers to pantothenic acid or its analogues or derivatives, such as calcium pantothenate, sodium pantothenate, etc.; vitamin B6 refers to pyridoxine or its analogues or derivatives; vitamin B7 is biotin or its analogues or derivatives; vitamin B9 refers to folic acid or its analogues or derivatives; vitamin B12 refers to cyanocobalamin or its analogues or derivatives; vitamin C refers to ascorbic acid or its analogues or derivatives, such as vitamin C palmitate, vitamin C sodium, vitamin C calcium, vitamin C potassium, and vitamin C magnesium phosphate and so on.

As used herein, the terms "analogs" and "analogues" refers to any two or more molecules or fragments that have roughly the same structure and have the same biological activity but can have different levels of activity. The term "derivative" used herein refers to a more complex compound derived from the replacement of a hydrogen atom or group of atoms in a compound by other atoms or groups of atoms.

BRIEF DESCRIPTION OF THE DRAWINGS

FIG. 1: Effects of single dose of 9 components multivitamin BC on the small intestinal propulsive rate in mice with loperamide-induced constipation.

FIG. 2: Effects of single dose of combination 1 or combination 2 (8 components multivitamin BC) on the small intestinal propulsive rate in mice with loperamide-induced constipation.

FIG. 3: Effects of single dose of combination 3 or combination 4 (8 components multivitamin BC) on the small intestinal propulsive rate in mice with loperamide-induced constipation.

FIG. 4: Effects of single dose of combination 5 or combination 6 (8 components multivitamin BC) on the small intestinal propulsive rate in mice with loperamide-induced constipation.

FIG. 5: Effects of single dose of combination 7, combination 8 or combination 9 (8 components multivitamin BC) on the small intestinal propulsive rate in mice with loperamide-induced constipation.

FIG. 6: Effects of single dose of multivitamin BC on the ATP content of energy metabolism of small intestinal in mice.

FIG. 7. Effects of multiple doses of multivitamin BC on small intestine propulsion function in mice with loperamide-induced constipation.

FIG. 8. Effects of multiple doses of 9 components multivitamin BC on the ATP content of energy metabolism of small intestinal in mice.

DETAILED DESCRIPTION

Example 1: Effects of Single Dose of 9 Components Multivitamin BC on the Small Intestinal Propulsive Rate in Mice with Loperamide-Induced Constipation 1.1 Experimental Methods The 20-25 g male mice of C57BL/6 were selected. The experimental animals were randomly divided into normal control group, loperamide model group, 9 components multivitamin BC low dose group (0.75×), multivitamin BC moderate dose group (1.5×) and multivitamin BC high dose group (3×). After fasting and freely drinking for about 22-24 hours, each group of the mice were intragastrically administrated at above doses at 20 ml/kg. After 30 minutes of administration, the control group was injected subcutaneously with the saline solution containing 1.0% Tween 80 while the other groups were injected subcutaneously with loperamide in an injection volume of 10 ml/kg. After a subcutaneous injection for 30 minutes, an intragastric administration of the charcoal solution was performed at an administration volume of 10 ml/kg. Twenty minutes after an intragastric administration of the charcoal solution, the animal was sacrificed by cervical dislocation and its abdominal cavity was immediately opened to separate the mesentery. The intestinal canal from the pylorus to the ileocecal junction was carefully removed and put on a tray. Be careful not to involve the small intestine, gently place the small intestine in a straight line, and measure the total length of the small intestine. The length from the pylorus to the front of the charcoal solution is the propulsive distance of the charcoal solution, and the small intestinal propulsive rate (%) of the charcoal solution was calculated. Small intestinal propulsive rate (%)=(the propulsive distance of the charcoal solution/the total length of the small intestine)×100%.

1.2 Experimental Drug

Composition list of multivitamin BC (mice):

| 9 components of multivitamin BC | | |
|---|---|---|
| No. | Components | Dose (1X mg/kg) |
| 1 | VB1 | 19.68 |
| 2 | VB2 | 10.25 |
| 3 | VB3 | 19.885 |
| 4 | VB5 | 21.32 |
| 5 | VB6 | 20.5 |
| 6 | VC | 30.75 |
| 7 | VB7 | 0.0205 |
| 8 | VB9 | 0.082 |
| 9 | VB12 | 0.0205 |

1.3 Experimental Results

The experimental results (FIG. 1) showed that the small intestinal propulsive rate in the model group was significantly lower than that in the control group. The small intestinal propulsive rate of mice was significantly increased after administration of the moderate dose of 9 components multivitamin BC. With the increase of the dose, the small intestinal propulsive effect of high dose 9 components multivitamin BC increased more obviously in a dose-dependent manner (N=16).

Example 2: Screening the Effect of 8 Components of Multivitamin BC Administration on the Small Intestinal Propulsive Rate in Mice with Loperamide-Induced Constipation 2.1 Experimental Methods The 8 component group is a combination of components removing any one component from the 9 components. They are 8-component combination 1 (removed B1), 8-component combination 2 (removed B2), 8-component combination 3 (removed B3), 8-component combination 4 (removed B5), 8-component combination 5 (removed B6)), 8-component combination 6 (removed VC), 8-component combination 7 (removed B7), 8-component combination 8 (removed B9), 8-component combination 12 (removed B12).

2.2 Experimental drug

| 8-component combination table 8-component combination of multivitamin BC | | |
|---|---|---|
| No. | Component was removed | Dose (1X mg/kg) |
| 1 | VB1 | 19.68 |
| 2 | VB2 | 10.25 |
| 3 | VB3 | 19.885 |
| 4 | VB5 | 21.32 |
| 5 | VB6 | 20.5 |
| 6 | VC | 30.75 |
| 7 | VB7 | 0.0205 |
| 8 | VB9 | 0.082 |
| 9 | VB12 | 0.0205 |

2.3 Experimental Results 2.3.1 Effects of Single Dose of Combination 1 or Combination 2 (8 Components Multivitamin BC) on the Small Intestinal Propulsive Rate in Mice with Loperamide-Induced Constipation.

The experimental results (FIG. 2) showed that the small intestinal propulsive rate in the model group was significantly lower than that in the normal control group. The small intestinal propulsive rate of mice was significantly higher than the model group after administration of the 9 components multivitamin BC. The small intestinal propulsive rate were improved to a certain extent after the administration of 8 components combination 1 or combination 2 (N=8-10).

2.3.2 Effects of single dose of combination 3 or combination 4 (8 components multivitamin BC) on the small intestinal propulsive rate in mice with loperamide-induced constipation.

The experimental results (FIG. 3) showed that the small intestinal propulsive rate in the model group was significantly lower than that in the normal control group. The small intestinal propulsive rate of mice was significantly higher than the model group after administration of the 9 components multivitamin BC. The small intestinal propulsive rate increased significantly after the administration of 8 components combination 3. The small intestinal propulsive rate were improved to a certain extent after the administration of 8 components combination 4 (removed vitamin B5) (N=8-10).

2.3.3 Effects of Single Dose of Combination 5 or Combination 6 (8 Components Multivitamin BC) on the Small Intestinal Propulsive Rate in Mice with Loperamide-Induced Constipation.

The experimental results (FIG. 4) showed that the small intestinal propulsive rate in the model group was significantly lower than that in the normal control group. The small intestinal propulsive rate of mice was significantly higher than the model group after administration of the 9 components multivitamin BC. The small intestinal propulsive rate were improved to a certain extent after the administration of 8 components combination 5 or combination 6 (N=8-10).

2.3.4 Effects of Single Dose of Combination 7 or Combination 8 or Combination 9 (8 Components Multivitamin BC) on the Small Intestinal Propulsive Rate in Mice with Loperamide-Induced Constipation.

The experimental results (FIG. 5) showed that the small intestinal propulsive rate in the model group was significantly lower than that in the normal control group. The small intestinal propulsive rate of mice was significantly higher than the model group after administration of the 9 components multivitamin BC. The small intestinal propulsive rate were improved to a certain extent after the administration of 8 components combination 7 or combination 8 or combination 9 (N=8-10).

Example 3: Effects of Single Dose of Multivitamin BC on the ATP Content of Energy Metabolism of Small Intestinal in Mice 3.1 Experimental Methods The 20-25 g male mice of C57BL/6 were selected. The experimental animals were randomly divided into normal control group, 9 components multivitamin BC low dose group (0.75×), multivitamin BC moderate dose group (1.5×) and multivitamin BC high dose group (3×). After fasting and freely drinking for about 22-24 hours, each group of the mice were intragastrically administrated at above doses at 20 ml/kg. After 30 minutes of administration, the animal was sacrificed by cervical dislocation. The upper intestinal tube about 3 cm from the pylorus was cutted, putted into normal saline for cleaning, and the chyme was removed. Then dry it with absorbent paper and put it into 1.5 ml EP tube for liquid nitrogen quick-freezing. After it was ground into powder in liquid nitrogen, ATP was extracted. The Phenol-TE (50 mg to 1 mL) was added, thoroughly mixed, and left for 10 min at room temperature. The supernatant was obtained after centrifuged at 12000 g for 10 min. 1 mL of sample was mixed with 200 uL chloroform and 600 uL deionized water, Oscillating 20 s mixed, centrifuged at 12000 g for 10 min to obtain the supernatant, and 20 uL sample was added to 100 uL ATP test solution (Kit of Biyuntian) to determine the luminescence value.

3.2 Experimental Results

The experimental results (FIG. 6) showed that the small intestinal ATP content of mice was increased after administration of 9 components of multivitamin BC, and compared with the normal group, the small intestinal ATP content of the high-dose group was significantly increased (N=35-39).

Example 4: Effects of Multiple Doses of Multivitamin BC on Small Intestine Propulsion Function in Mice with Loperamide-Induced Constipation.

4.1 Experimental Methods

The 20-25 g male mice of C57BL/6 were selected. The experimental animals were randomly divided into normal control group, loperamide model group, 9 components multivitamin BC low dose group (0.75×), multivitamin BC moderate dose group (1.5×) and multivitamin BC high dose group (3×). The administration was continued for seven days, and the daily dose was divided into two doses, once in the morning and once in the afternoon. After fasting and freely drinking for about 22-24 hours from the 8th day, each group of the mice were intragastrically administrated at above doses at 20 ml/kg. After 30 minutes of administration, the animals were injected subcutaneously with 2.5 mg/kg loperamide (in saline solution containing 1.0% Tween 80) in an injection volume of 10 ml/kg. After a subcutaneous injection for 30 minutes, an intragastric administration of the charcoal solution was performed at an administration volume of 10 ml/kg. Twenty minutes after an intragastric administration of the charcoal solution, the animal was sacrificed by cervical dislocation and its abdominal cavity was immediately opened to separate the mesentery. The intestinal canal from the pylorus to the ileocecal junction was carefully removed and put on a tray. Be careful not to involve the small intestine, gently place the small intestine in a straight line, and measure the total length of the small intestine. The length from the pylorus to the front of the charcoal solution is the propulsive distance of the charcoal solution, and the small intestinal propulsive rate (%) of the charcoal solution was calculated. Small intestinal propulsive rate (%)=(the propulsive distance of the charcoal solution/the total length of the small intestine)×100%.

4.2 Experimental Results

The experimental results (FIG. 7) showed that the small intestinal propulsive rate in the model group was significantly lower than that in the normal control group. The small intestinal propulsive rate of mice was significantly increased after administration of multiple doses of 9 components multivitamin BC. The small intestinal propulsive effect of low dose 9 components multivitamin BC was equivalent to the high dose (N=30).

Example 5: Effects of Multiple Doses of 9 Components Multivitamin BC on the ATP Content of Energy Metabolism of Small Intestinal in Mice 5.1 Experimental Methods The 20-25 g male mice of C57BL/6 were selected. The experimental animals were randomly divided into normal control group, loperamide model group, 9 components multivitamin BC low dose group (0.75×), multivitamin BC moderate dose group (1.5×) and multivitamin BC high dose group (3×). The administration was continued for seven days, and the daily dose was divided into two doses, once in the morning and once in the afternoon. After fasting and freely drinking for about 22-24 hours from the 8th day, each group of the mice were intragastrically administrated at above doses at 20 ml/kg. The animal was sacrificed by cervical dislocation thirty minutes later. The upper intestinal tube about 3 cm from the pylorus was cutted, putted into normal saline for cleaning, and the chyme was removed. Then dry it with absorbent paper and put it into 1.5 ml EP tube for liquid nitrogen quick-freezing. After it was ground into powder in liquid nitrogen, ATP was extracted. The Phenol-TE (50 mg to 1 mL) was added, thoroughly mixed, and left for 10 min at room temperature. The supernatant was obtained after centrifuged at 12000 g for 10 min. 1 mL of sample was mixed with 200 uL chloroform and 600 uL deionized water, Oscillating 20 s mixed, centrifuged at 12000 g for 10 min to obtain the supernatant, and 20 uL sample was added to 100 uL ATP test solution (Kit of Biyuntian) to determine the luminescence value.

5.2 Experimental Results

The experimental results (FIG. 8) showed that the small intestinal ATP content of mice was increased after administration of multiple doses of 9 components multivitamin BC, and compared with the normal group, the small intestinal ATP content of the high-dose group was significantly increased (N=36-40). It showed that multivitamin BC may treat constipation by improving the energy metabolism in the small intestine.

Example 6: Preparation Process of Multivitamin BC Three-Layer Tablet

6.1 Preparation of the Total Mixed Granulations of the First Layer

6.1.1 VB1 VB2/VB3/VB6 Granulations

TABLE 1 the formula of VB1/VB2/VB3/VB6 granulations

| component | mg/tablet |
| --- | --- |
| VB1 | 48 |
| VB2 | 25 |
| VB3 | 48 |
| VB6 | 50 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

6.1.2 Folic Acid Granulations

TABLE 2 the formula of folic acid granulations

| component | mg/tablet |
| --- | --- |
| Folic acid | 0.2 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

6.1.3 VB12 Granulations

TABLE 3 the formula of VB12 granulations

| component | mg/tablet |
| --- | --- |
| VB12 | 0.05 |

Microcrystalline, silicon dioxide, gelatin, and other excipients were added to prepare binders and load drug.

6.1.4 Mixing Process

TABLE 4 the formula of the total mixed granulations of the first layer

| component | mg/tablet |
| --- | --- |
| VB1/VB2/VB3/VB6 granulations | 392.5 |
| folic acid granulations | 48.0 |
| VB12 granulations | 53.71 |

Microcrystalline, silicon dioxide, magnesium stearate, and other excipients were mixed to obtain the first layer of total mixed granulations.

6.2 Preparation of the Total Mixed Granulations of the Second Layer

6.2.1 VC Granulations

TABLE 5 the formula of VC granulations

| component | mg/tablet |
| --- | --- |
| VC | 75 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

6.2.2 Calcium Pantothenate Granulations

TABLE 6 the formula of calcium pantothenate granulations

| component | mg/tablet |
| --- | --- |
| calcium pantothenate | 52 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

6.2.3 Mixing Process

TABLE 7 the formula of the total mixed granulations of the second layer

| component | mg/tablet |
| --- | --- |
| VC granulations | 183.6 |
| calcium pantothenate granulations | 196.13 |

Sodium carboxymethyl starch, silicon dioxide, magnesium stearate, and other excipients were mixed to obtain the second layer of total mixed granulations.

6.3 the Total Mixed Granulations of the Third Layer

6.3.1 Biotin Granulations

TABLE 8 the formula of biotin granulations

| component | mg/tablet |
| --- | --- |
| biotin | 0.05 |

Microcrystalline cellulose, mannitol, sodium carboxymethyl starch, povidone K30, and other excipients were premixed. The granulations were transferred to a fluidized bed for coating, and 15% (w/w) coating fluid was added, the weight of the granulations increased 20% theoretically.

6.3.2 the Blank Granulations

The blank granulations were prepared as follows: Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

6.3.3 Mixing Process

TABLE 9

| the formula of the total mixed granulations of the third layer | |
|---|---|
| component | mg/tablet |
| biotin granulations | 63.78 |
| blank granulations | 172.75 |

Sodium carboxymethyl starch, silicon dioxide, magnesium stearate, and other excipients were mixed to obtain the third layer of total mixed granulations.

6.4 the Preparation of the Three Layers Tablet

The total mixed granulations of the first layer were poured into the first material funnel of the three-layer tablet machine, operating the tablet press, and adjusting the parameters so that the tablet weight reached ±5% of the target tablet weight. Then the total mixed granulations of the second layer were poured into the second material funnel, adjusting the parameters so that the total weight (the first layer piece+the second layer piece) reached ±5% of the target tablet weight. Finally the total mixed granulations of the third layer were poured into the third material funnel, adjusting the parameters so that the total weight (the first layer piece+the second layer piece+the third layer piece) reached ±5% of the target piece weight. After the weight and hardness of the three-layer tablet were stabilized, the tablet was formally compressed.

6.5 Coating

The core was putted into the coating pan. The coating weight was increased by 3%~4%.

6.6 Packaging

Example 7: Preparation of Multivitamin BC Capsule 7.1 the First Type of Tablet (VB Tablet)

7.1.1 the Granulations of VB1/VB2/VB3/VB6

TABLE 10

| The formula of VB1/VB2/VB3/VB6 granulations | |
|---|---|
| component | mg/tablet |
| VB1 | 8 |
| VB2 | 4.17 |
| VB3 | 8 |
| VB6 | 8.33 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

7.1.2 Folic Acid Granulations

TABLE 11

| the formula of folic acid granulations | |
|---|---|
| component | mg/tablet |
| Folic acid | 0.33 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

7.1.3 VB12 Granulations

TABLE 12

| the formula of VB12 granulations | |
|---|---|
| component | mg/tablet |
| VB12 | 0.0083 |

Microcrystalline, silicon dioxide, gelatin, and other excipients were added to prepared binders and load drug.

7.1.4 Mixing Process and Tabletting

TABLE 13

| the formula of the total mixed granulations of the VB tablet | |
|---|---|
| component | mg/tablet |
| VB1/VB2/VB3/VB6 granulations | 65.42 |
| folic acid granulations | 8.00 |
| VB12 granulations | 8.95 |

Sodium carboxymethyl starch, silicon dioxide, magnesium stearate, and other excipients were added. The total mixed granulations of VB tablets were obtained by weight according to the prescription. The total mixed granulations were poured into a tablet machine, and formally started tabletting after the tablet weight and hardness were stable to obtain VB tablets.

7.2 the Second Type of Tablet (VC/P Tablet)

7.2.1 VC Granulations

TABLE 14

| the formula of VC granulations | |
|---|---|
| component | mg/tablet |
| VC | 18.75 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

7.2.2 Calcium Pantothenate Granulations

TABLE 15 the formula of VC granulations

| component | mg/tablet |
|---|---|
| calcium pantothenate | 13 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

7.2.3 Mixing Process and Tabletting

TABLE 16 the formula of the total mixed granulations of the VC/P tablet

| component | mg/tablet |
|---|---|
| VC granulations | 45.9 |
| calcium pantothenate granulations | 49.03 |

Sodium carboxymethyl starch, silicon dioxide, magnesium stearate, and other excipients were added, mixed to form the total mixed granulations of the VC/P tablet. The total mixed granulations were poured into a tablet machine, and formally started tabletting after the tablet weight and hardness were stable to obtain VC/P tablets.

7.3 the Third Type of Tablet (Biotin Tablet)

7.3.1 Biotin Granulations

TABLE 17 the formula of biotin granulations

| component | mg/tablet |
|---|---|
| biotin | 0.025 |

Microcrystalline cellulose, mannitol, sodium carboxymethyl starch, povidone K30, other excipients, and film coating were premixed. The granulations were transferred to a fluidized bed for coating, and 15% (w/w) coating fluid was added, The weight of the granulations increased 20% theoretically.

7.3.2 Mixing Process and Tabletting

TABLE 18 the formula of the total mixed granulations of the biotin

| component | mg/tablet |
|---|---|
| biotin granulations | 76.80 |

Sodium carboxymethyl starch, silicon dioxide, magnesium stearate, and other excipients were added, mixed to form the total mixed granulations of the biotin. The total mixed granulations were poured into a tablet machine, and formally started tabletting after the tablet weight and hardness were stable to obtain biotin tablets.

7.4 Coating

The core was putted into the coating pan and the coating weight was increased by 3%-4%.

7.5 Filling Capsules

By using a capsule filling machine, 3 VB tablets, 2 VC/P tablets and one biotin tablet were filled into the one capsule.

7.6 Packaging

High density polyethylene bottle or blister were used for packaging.

Example 8: Preparation of Multivitamin BC Three Types of Tablets

8.1 the First Type of Tablet

8.1.1 VB1 VB2/VB3/VB6 Granulations

TABLE 19 the formula of VB1/VB2/VB3/VB6 granulations

| component | mg/tablet |
|---|---|
| VB1 | 48 |
| VB2 | 25 |
| VB3 | 48 |
| VB6 | 50 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

8.1.2 Folic Acid Granulations

TABLE 20 the formula of folic acid granulations

| component | mg/tablet |
|---|---|
| Folic acid | 0.2 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

8.1.3 VB12 Granulations

TABLE 21 the formula of VB12 granulations

| component | mg/tablet |
|---|---|
| VB12 | 0.05 |

Microcrystalline, silicon dioxide, gelatin, and other excipients were added to prepare binders and load drug.

8.1.4 Mixing Process

TABLE 22

| the formula of the total mixed granulations of the first type of tablet | |
|---|---|
| component | mg/tablet |
| VB1/VB2/VB3/VB6 granulations | 392.5 |
| folic acid granulations | 48.0 |
| VB12 granulations | 53.71 |

Microcrystalline, silicon dioxide, magnesium stearate, and other excipients were mixed to obtain the first type of tablet of total mixed granulations.

8.1.5 Mixed the Total Mixed Granules and Tabletting 8.1.6 Coating

The tablets were coated with a transparent film, and the weight after coating increased by 1.5%-4%.

8.2 the Second Type of Tablet 8.2.1 VC Granulations

TABLE 23

| the formula of VC granulations | |
|---|---|
| component | mg/tablet |
| VC | 75 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

8.2.2 Calcium Pantothenate Granulations

TABLE 24

| the formula of calcium pantothenate granulations | |
|---|---|
| component | mg/tablet |
| calcium pantothenate | 52 |

Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

8.2.3 Mixing Process

TABLE 25

| the formula of the total mixed granulations of the second type of tablet | |
|---|---|
| component | mg/tablet |
| VC granulations | 183.6 |
| calcium pantothenate granulations | 196.125 |

Sodium carboxymethyl starch, silicon dioxide, magnesium stearate, and other excipients were mixed to obtain the second type of tablet of total mixed granulations.

8.2.4 Mixed the Total Mixed Granules and Tabletting 8.2.5 Coating

The tablets were coated with a transparent film, and the weight after coating increased by 1.5%-4%.

8.3 the Third Type of Tablet 8.3.1 Biotin Granulations

TABLE 26

| the formula of biotin granulations | |
|---|---|
| component | mg/tablet |
| biotin | 0.05 |

Microcrystalline cellulose, mannitol, sodium carboxymethyl starch, povidone K30, other excipients, and film coating were premixed. The granulations were transferred to a fluidized bed for coating, and 15% (w/w) coating fluid was added. The weight of the granulations was increased 20% theoretically.

8.3.2 the Blank Granulations

The blank granulations were prepared as follows: Microcrystalline cellulose, mannitol, sodium carboxymethyl starch, povidone K30, and other excipients were added to pretreat raw materials and prepare binders. The materials were mixed in dry conditions for 10 minutes. Soft materials were obtained by wet granulation. Then the product was obtained by wet screening, drying and granulation.

8.3.3 Mixing Process

TABLE 27

| the formula of the total mixed granulations of the third type of tablet | |
|---|---|
| component | mg/tablet |
| biotin granulations | 63.78 |
| blank granulations | 172.75 |

Sodium carboxymethyl starch, silicon dioxide, and magnesium stearate were mixed to obtain the third type of tablet of total mixed granulations.

8.3.4 Mixed the Total Mixed Granules and Compressed Tablets 8.3.5 Coating

The tablets were coated with a transparent film, and the weight after coating increased by 1.5%-4%.

8.4 Package

Putted the three types of tablets into bottles respectively.

Example 9: Study on the Stability of Multivitamin BC 9.1 Stability Study of Monolayer Tablet VC granulations and VB1/VB2/VB3/VB6/calcium pantothenate/choline ditartrate/folic acid/biotin/VB12 granulations were mixed according to the proportion of the three multivitamin BC tablets, and were compressed into monolayer tablets, and the stability was preliminarily tested. The detection methods for each component are listed below:

9.1.1 Test Methods for VB12 and Biotin

TABLE 28

| HPLC system for the detection of VB12 and biotin | |
|---|---|
| System | The HPLC system includes a pump, an automatic sampler, and a column thermostat |
| chromatographic column | Agilent ZORBAX SB-C18, 4.6 × 150 mm, 5-micron |
| Detector | DAD detector, detection wavelength, 210 nm, 360 nm |

9.1.2 Test Methods for Folic Acid

TABLE 29

| HPLC system for the detection of folic acid | |
|---|---|
| System | The HPLC system includes a pump, an automatic sampler, and a column thermostat |
| chromatographic column | Waters Atlantis ®T3, 4.6 × 250 mm, 5-micron |
| Detector | DAD detector, detection wavelength, 300 nm |

9.1.3 Test Methods for Calcium Pantothenate

TABLE 30

| HPLC system and chromatographic parameters for the detection of calcium pantothenate | |
|---|---|
| System | The HPLC system includes a pump, an automatic sampler, and a column thermostat |
| chromatographic column | Waters Atlantis ®T3, 4.6 × 250 mm, 5-micron |
| ultraviolet detector | DAD detector, detection wavelength, 210 nm |

9.1.4 Test Methods for VB1, VB2, VB3, and VB6

TABLE 31

| HPLC system and chromatographic parameters for the detection of folic acid | |
|---|---|
| System | The HPLC system includes a pump, an automatic sampler, and a column thermostat |
| chromatographic column | Waters Atlantis ®T3, 4.6 × 250 mm, 5-micron |
| Detector | DAD detector, detection wavelength, 280 nm |

9.1.5 Test Methods for VC

Twenty tablets were grinded thoroughly. The powder equivalent to about 0.2 g of vitamin C of the test substance was weight accurately, putted into an iodine bottle, accurately measured freshly boiled water and diluted acetic acid into the iodine bottle, oscillation the bottle after ultrasonic vibration for 5 minutes, filtered quickly, accurately measured 50 mL of the filtrate and putted it into another iodine bottle, added titration indicator into the bottle, and titrated with iodine titrant immediately after oscillating until the solution turning blue and did not fade within 30 s.

Results: The content of folic acid, biotin, VB12 and VB1 decreased in the intermediate and long-term conditions for 2 months, and the remaining components were basically stable. It indicated that the interaction between the components in the monolayer tablet may be exist except for the possibility of self-degradation, and the formulation preparation process needs to be developed again.

TABLE 32

The content of each component in the stability test of multivitamin BC monolayer tablets

| Name | component | 0 Day | −20° C./ 2 months | 4° C./ 2 months | long-term conditions/ 2 months | intermediate/ 2 months |
|---|---|---|---|---|---|---|
| VBC monolayer tablets | folic acid | 97% | 95% | 92% | 86% | 76% |
| | biotin | 101% | 102% | 98% | 89% | 79% |
| | VB12 | 97% | 102% | 101% | 99% | 90% |
| | niacin | 99% | 103% | 97% | 97% | 102% |
| | VB6 | 97% | 101% | 101% | 103% | 102% |
| | VB1 | 97% | 102% | 101% | 93% | 84% |
| | VB2 | 98% | 101% | 102% | 102% | 101% |
| | VC | 97% | 100% | 100% | 97% | 96% |
| | calcium pantothenate | 114% | 102% | 102% | 98% | 93% |
| | choline bitartrate | 108% | 93% | 94% | 96% | 96% |

9.2 Stability Study of Three-Layer Tablets

The three-layer multivitamin BC tablets were produced according to the preparation process in Example 6, the test method of each component was the same as that of the monolayer tablet, and the content results of the stability test (3.5 months) were showed below:

TABLE 33

The content of each component in the stability test of multivitamin BC three-layer tablets

| Name | component | 0 day | 4° C./ 2 month | long-term conditions/ 2 months | intermediate/ 2 months | accelerated/ 2 months |
|---|---|---|---|---|---|---|
| VBC three-layer tablets | VC | 99.94% | 99.70% | 99.15% | 98.36% | 100.87% |
| | VB1 | 99.63% | 99.22% | 98.73% | 96.90% | 98.49% |
| | VB2 | 99.50% | 102.49% | 101.99% | 99.47% | 101.27% |
| | VB3 | 99.47% | 101.63% | 101.17% | 99.02% | 100.55% |
| | VB6 | 99.90% | 102.70% | 103.36% | 101.47% | 101.37% |
| | folic acid | 99.63% | 99.66% | 98.47% | 100.87% | 99.80% |
| | calcium pantothenate | 101.46% | 101.68% | 101.44% | 101.42% | 101.12% |
| | biotin | 98.21% | 98.43% | 84.73% | 78.61% | 69.04% |
| | VB12 | 101.93% | 103.68% | 102.37% | 102.74% | 99.45% |

9.3 Study on the Stability of Multivitamin Capsules

The multivitamin BC capsules were produced according to the preparation process in Example 7, the test method of each component was the same as that of the monolayer tablet, and the content results of the stability test were showed below:

TABLE 34

The content of each component in the stability test of multivitamin BC capsules

| Name | component | 0 month | intermediate/ 2 months | accelerated/ 2 months | long-term/ 3 months | intermediate/ 3 months |
|---|---|---|---|---|---|---|
| VBC capsules | biotin | 99.19% | 97.46% | 93.86% | 97.72% | 95.61% |
| | VC | 97.06% | 96.25% | 97.00% | 97.46% | 97.04% |
| | calcium pantothenate | 102.10% | 102.36% | 102.06% | 101.17% | 102.05% |
| | VB12 | 102.67% | 100.33% | 95.41% | 99.68% | 99.38% |
| | folic acid | 101.81% | 102.59% | 101.41% | 102.94% | 101.12% |
| | VB1 | 93.78% | 94.07% | 90.84% | 93.02% | 97.83% |
| | VB2 | 94.57% | 94.28% | 93.05% | 93.42% | 97.23% |
| | VB3 | 92.10% | 93.33% | 91.67% | 92.39% | 93.42% |
| | VB6 | 93.66% | 93.18% | 91.24% | 91.64% | 88.39% |

9.4 Stability Study of Three Types of Tablets

The multivitamin BC three types of tablets were produced according to the preparation process in Example 8, the detection method of each component was the same as that of the monolayer tablet, and the content results of the stability test were showed below:

TABLE 35

The content of each component in the stability test of multivitamin BC three types of tablet

| Name | Component | 0 day | accelerated/1 months | accelerated/2 months | accelerated/3 months |
|---|---|---|---|---|---|
| VBC three types of tablets | VB12 | 101.69% | 100.12% | 96.99% | 98.32% |
| | folic acid | 101.66% | 99.02% | 98.61% | 97.63% |
| | VB1 | 102.21% | 96.72% | 94.58% | 95.43% |
| | VB2 | 103.08% | 103.49% | 102.54% | 103.95% |
| | niacinamide | 102.56% | 101.37% | 97.51% | 97.13% |
| | VB6 | 101.45% | 97.19% | 95.60% | 97.17% |
| | VC | 94.54% | 94.75% | 94.14% | 94.58% |
| | calcium pantothenate | 99.06% | 100.82% | 98.60% | 100.19% |
| | biotin | 98.84% | 100.33% | 96.60% | 97.10% |

CONCLUSIONS

The results of the small intestine propulsion experiment in the treatment of constipated mice by a single dose of 9 components of multivitamin BC showed that 9 components multivitamin BC could effectively restore the small intestinal propulsion rate of constipated mice in the dose-dependent manner and could improve the propulsion function of the small intestine of constipated mice to treat constipation.

The results of the small intestine propulsion experiment in the treatment of constipated mice by a single dose of 8 components of multivitamin BC showed that the small intestinal propulsive rate were improved to a certain extent after the administration of any 8 components of multivitamin BC (The components of VB1, VB2, VB3, VB5, VB6, VB7, VB9, VC, VB12 was removed separately).

Compared with multivitamin BC monolayer tablet product, the three-layer tablet multivitamin BC product, the multivitamin BC capsule product and the three types of tablets of multivitamin BC product have a more stable content of each component. The content of VB1, folic acid, VB12 and biotin in the monolayer tablets decreased significantly, while were no obvious decreased in the three-layer tablet product, the capsule product and the three types of multivitamin BC tablets product. It showed that the preparation process of three-layer tablets, capsules and three types of multivitamin BC tablets product could avoid the mutual influence caused by the contact of each component, and effectively ensure the stability of each component.

In order to describe and understand the present invention more clearly, we describe the present invention by examples in detail. It is clear that modification and alterations of the present invention will be apparent to those skilled in the art without departing from the scope and spirit of the present invention.

What is claimed is:

1. A multivitamin tablet comprising a first layer, a second layer, and a third layer; wherein the second layer is located between the first layer and the third layer; and wherein each layer consists of
   (i) one or more active components; and
   (ii) one or more excipients;
   wherein the one or more active components in the first layer consist of vitamin B1, vitamin B2, vitamin B3, vitamin B6, vitamin B12, and folic acid; the one or more active components in the second layer consist of vitamin C and calcium pantothenate; and the one or more active components in the third layer consist of biotin.

2. The multivitamin tablet according to claim 1, wherein the one or more excipients is selected from a filler, a binder, a disintegrant, a glidant, and a lubricant.

3. The multivitamin tablet according to claim 1, wherein the one or more excipients in each of the first layer, the second layer, and the third layer comprise microcrystalline cellulose, mannitol, sodium carboxymethyl starch, and povidone K30.

4. The multivitamin tablet according to claim 3, wherein the one or more excipients in the first layer further comprise silicon dioxide, gelatin, and magnesium stearate.

5. The multivitamin tablet according to claim 1, wherein the tablet further comprises a coating of a transparent film.

* * * * *